US010995322B2

(12) United States Patent
Sanghani et al.

(10) Patent No.: US 10,995,322 B2
(45) Date of Patent: May 4, 2021

(54) PROCESSES TO PREPARE ELONGATED 2-KETOACIDS AND C5-C10 COMPOUNDS THEREFROM VIA GENETIC MODIFICATIONS TO MICROBIAL METABOLIC PATHWAYS

(71) Applicant: Dow Global Technologies LLC, Midland, MI (US)

(72) Inventors: Paresh C. Sanghani, Indianapolis, IN (US); Sarah Delaplane, Indianapolis, IN (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 16/338,098

(22) PCT Filed: Dec. 30, 2016

(86) PCT No.: PCT/US2016/069430
§ 371 (c)(1),
(2) Date: Mar. 29, 2019

(87) PCT Pub. No.: WO2018/063423
PCT Pub. Date: Apr. 5, 2018

(65) Prior Publication Data
US 2019/0249151 A1 Aug. 15, 2019

Related U.S. Application Data

(60) Provisional application No. 62/402,586, filed on Sep. 30, 2016, provisional application No. 62/402,569, filed on Sep. 30, 2016.

(51) Int. Cl.
| | |
|---|---|
| *C12N 1/19* | (2006.01) |
| *C12N 9/88* | (2006.01) |
| *C12N 15/00* | (2006.01) |
| *C12N 15/70* | (2006.01) |
| *C12P 7/42* | (2006.01) |
| *C12N 9/10* | (2006.01) |
| *C12P 7/04* | (2006.01) |
| *C12P 7/24* | (2006.01) |
| *C12P 7/40* | (2006.01) |
| *C12N 9/04* | (2006.01) |
| *C12P 7/44* | (2006.01) |
| *C12N 15/52* | (2006.01) |
| *C12N 9/02* | (2006.01) |
| *C12P 5/02* | (2006.01) |

(52) U.S. Cl.
CPC ......... *C12N 9/1025* (2013.01); *C12N 9/0006* (2013.01); *C12N 9/0008* (2013.01); *C12N 9/88* (2013.01); *C12N 15/52* (2013.01); *C12P 5/02* (2013.01); *C12P 7/04* (2013.01); *C12P 7/24* (2013.01); *C12P 7/40* (2013.01); *C12P 7/44* (2013.01); *C12Y 101/01085* (2013.01); *C12Y 102/01048* (2013.01); *C12Y 203/03013* (2013.01); *C12Y 402/01033* (2013.01)

(58) Field of Classification Search
CPC ...... C12P 7/42; C12P 7/50; C12P 7/62; C12N 15/70; C12N 9/0004; C12N 9/1025; C12N 9/1022; C12N 15/74; C12N 9/16; C12Y 203/03013; C12Y 401/01006; C12Y 402/01033
USPC ......... 435/252.3, 320.1, 142, 147, 212, 196, 435/143
See application file for complete search history.

(56) References Cited

U.S. PATENT DOCUMENTS

| | | |
|---|---|---|
| 8,232,089 B2 | 7/2012 | Urano et al. |
| 8,298,798 B2 | 10/2012 | Liao et al. |
| 2011/0201083 A1 | 8/2011 | Liao et al. |
| 2012/0070868 A1 | 3/2012 | Lee et al. |
| 2014/0377857 A1 | 12/2014 | Liao et al. |
| 2015/0259710 A1 | 9/2015 | Dundon et al. |
| 2016/0355850 A1 | 12/2016 | Sanghani et al. |
| 2017/0232043 A1 | 8/2017 | Falb et al. |
| 2017/0369863 A1 | 12/2017 | Sanghani et al. |

FOREIGN PATENT DOCUMENTS

| | | |
|---|---|---|
| WO | 2009046375 A2 | 4/2009 |
| WO | 2009096370 A1 | 8/2009 |
| WO | 2010045629 A2 | 4/2010 |

(Continued)

OTHER PUBLICATIONS

Devos et al., (Proteins: Structure, Function and Genetics, 2000, vol. 41: 98-107.*
Whisstock et al., (Quarterly Reviews of Biophysics 2003, vol. 36 (3): 307-340.*
Witkowski et al., (Biochemistry 38:11643-11650, 1999.*
Kisselev L. (Structure, 2002, vol. 10: 8-9.*
Atsumi et al., "Non-Fermentative Pathways for Synthesis of Branched-Chain Higher Alcohols as Biofuels", Nature, 2008, vol. 451, 86-90, Nature Publishing Group.
Becker et al., "Bio-Based Production of Chemicals, Materials and Fuels—Corynebacterium Glutamicum as Versatile Cell Factory", Current Opinion in Biotechnology, 2012, 23, 631-640, Elsevier.

(Continued)

*Primary Examiner* — Robert B Mondesi
*Assistant Examiner* — Mohammad Y Meah
(74) *Attorney, Agent, or Firm* — Dinsmore & Shohl LLP

(57) ABSTRACT

Genetically modified isopropylmalate synthases, processes for preparing a $C_7$-$C_{11}$ 2-ketoacids utilizing genetically modified isopropylmalate synthases, and microbial organisms including genetically modified isopropylmalate synthases are described. The genetically modified isopropylmalate synthases, processes for preparing a $C_7$-$C_{11}$ 2-ketoacids, and microbial organisms including genetically modified isopropylmalate synthases can be particularly useful for producing corresponding $C_{n-1}$ aldehydes, alcohols, carboxylic acids, and $C_{n-2}$ alkanes both in vivo and in vitro.

7 Claims, 6 Drawing Sheets

Specification includes a Sequence Listing.

(56) References Cited

FOREIGN PATENT DOCUMENTS

| WO | 2012135731 A2 | 10/2012 |
|---|---|---|
| WO | 2015089127 A1 | 6/2015 |

OTHER PUBLICATIONS

Becker et al., "Systems and Synthetic Metabolic Engineering for Amino Acid Production—The Heartbeat of Industrial Strain Development", Current Opinion in Biotechnology, 2012, 23, 718-726, Elsevier.
Choi et al., "Microbial Production of Short-Chain Alkanes", Nature, 2013, 502, 571-576, Macmillan Publishers.
Datsenko et al., "One-Step Inactivation of Chromosomal Genes in *Escherichia coli* K-12 Using PCR Products", Proc. Natl. Acad. Sci. USA, 2000, 97:12, 6640-6645.
Gronenberg et al., "Next Generation Biofuel Engineering in Prokaryotes", Current Opinion in Biotechnology, 2013, 17, 462-471, Elsevier.
Holton et al., "Structural Characterization of a D-Isomer Specific 2-Hydroxyacid Dehydrogenase from Lactobacillus Delbrueckii ssp. *bulgaricus*", Journal of Structural Biology, 2013, 181, 179-184, Elsevier Inc.
Hummel, Werner, "Large-Scale Applications of NAD(P)-Dependent Oxidoreductases: Recent Developments", Tibtech, 1999, 17, 487-492, Elsevier Science Ltd.
Koon et al., "Crystal Structure of LeuA from Mycobacterium Tuberculosis, a Key Enzyme in Leucine Biosynthesis", Proc. Natl. Acad. Sci. USA, 2004, 101:22, 8295-8300.
Manikandan et al., "Structural Studies on the Enzyme Complex Isopropylmalate Isomerase [LeuCD] from Mycobacterium Tuberculosis", Proteins, 2010, 35-49, Wiley-Liss, Inc.
Spaepen et al., "Characterization of Phenylpyruvate Decarboxylase, Involved in Auxin Production of Azospirillum Brasilense", Journal of Bacteriology, 2007, 189:21, 7626-7633.
Vedha-Peters et al., "Creation of a Broad-Range and Highly Stereoselective D-Amino Acid Dehydrogenase for the One-Step Synthesis of D-Amino Acids", J. Am. Chem. Soc., 2006, 128, 10923-10929, American Chemical Society.
Versees et al., "The Crystal Structure of Phenylpyruvate Decarboxylase from Azospirillum Brasilense at 1.5 A Resolution Implications for its Catalytic and Regulatory Mechanism", The FEBS Journal, 2007, 274, 2363-2375, The Authors Journal compilation.
Xiong et al., "A Bio-Catalytic Approach to Aliphatic Ketones", Scientific Reports, 2:311, doi: 10.1035/srep0311.
Zhang et al., "A Synthetic Metabolic Pathway for Production of the Platform Chemical Isobutyric Acid", ChemSusChem, 2011, 4, 1068-1070 Wiley-VCH Verlag GmbH & Co.
International Search Report and Written Opinion pertaining to PCT/US2015/064879 dated Mar. 22, 2016.
International Search Report and Written Opinion pertaining to PCT/US2016/069430 dated Jul. 4, 2017.
International Search Report and Written Opinion pertaining to PCT/US2016/069476 dated Jul. 4, 2017.
Felnagle et al., "Engineering Synthetic Recursive Pathways to Generate Non-Natural Small Molecules", Nature Chemical Biology, Jun. 2012, 518-526, vol. 8, Nature America, Inc.
Han et al., "Sites and Mechanisms of Aconitase Inactivation by Peroxynitrite: Modulation by Citrate and Glutathione", Biochemistry, 2005, 11986-11996, 44, American Chemical Society.
Hsu et al., "Leucine Biosynthesis in *Saccharomyces cerevisiae*, Purification and Characterization of b-Isopropylmalate Dehydrogenase", The Journal of Biological Chemistry, 1980, 7255-7260, vol. 255 No. 15.
Imada et al., "Structure of 3-Isopropylmalate Dehydrogenase in Complex with 3-Isopropylmalate at 2.0 A Resolution: the Role of Glu88 in the Unique Substrate-Recognition Mechanism", Structure, Aug. 1998, 971-982, 6, Current Biology Publications ISSN 0969-2126.
International Search Report and Written Opinion dated Mar. 18, 2015 pertaining to International Application No. PCT/US2014/069438.
Lee et al., "Metabolic Engineering of Clostridium Acetobutylicum M5 for Highly Selective Butanol Production", Biotechnology Journal, 2009, 1432-1440, 4, Wiley-VCH Verlag GmbH & Co.
Marcheschi et al., "A Synthetic Recursive '+1' Pathway for Carbon Chain Elongation", ACS Chemical Biology, 2012, 689-697, 7, American Chemical Society.
Sanghani et al., "Kinetic Mechanism of Human Glutathione-Dependent Formaldehyde Dehydrogenase", Biochemistry, 2000, 10720-10729, 39, American Chemical Society.
Shen et al., "A Synthetic Iterative Pathway for Ketoacid Elongation", Methods in Enzymology, 2011, 469-481, 497, Elsevier Inc.
Wang et al., "Optimization of Butanol Production from Tropical Maize Stalk Juice by Fermentation with Clostridium Beijerinckii NCIMB 8052", Bioresource Technology, 2011, 9985-9990, 102, Elsevier Ltd.
Zhang et al., "Expanding Metabolism for Biosynthesis of Non-natural Alcohols", PNAS, Dec. 2008, 20653-20658, vol. 105 No. 52, The National Academy of Science of the USA.
Rude et al., "New Microbial Fuels: A Biotech Perspective", Current Opinion in Microbiology, 2009, 274-281.
Zhang et al., "Subdomain II of alpha-isopropylmalate synthase is essential for activity: inferring a mechanism of feedback inhibition", The Journal of biological chemistry 2014, 289, 27966-27978.
Office Action pertaining to U.S. Appl. No. 15/030,616 dated Sep. 13, 2017.
Office Action pertaining to U.S. Appl. No. 15/533,390, dated Jun. 6, 2018.
Office Action dated Feb. 24, 2021 pertaining to U.S. Appl. No. 16/337,072, filed Mar. 27, 2019, 29 pgs.
Sadowski, M.I. et al., "The sequence-structure relationship and protein function prediction" Current Opinion in Structural Biology, ScienceDirect, Elsevier, 19: 357-362, 2009.
Tang, S. et al., Identification of Dehalobacter reductive dehalogenases that catalyse dechlorination of chloroform, 1,1,1-trichloroethane and 1,1-dichloroethane, Philosophical Transactions of the Royal Society, 368:20120318, pp. 1-10, 2013.
Seffernick, J. et al., "Melamine Deaminase and Atrazine Chlorohydrolase: 98 Percent Identical but Functionally Different" Journal of Bacteriology, vol. 183, No. 8, pp. 2405-2410, 2001.
Branden, C. et al., Introduction to Protein Structure, Garland Publishing Inc., New York, p. 247, 1991.

* cited by examiner

FIG. 3

| | |
|---|---|
| 614 | MSQQVIIFDTTLRDGEQALQASLSVKEKLQIALALERMGVDVMEVGFPVSSPGDFESV |
| 1409 | MSQQVIIFDTTLRDGEQALQASLSVKEKLQIALALERMGVDVMEVGFPVSSPGDFESV |
| 1414 | MSQQVIIFDTTLRDGEQALQASLSVKEKLQIALALERMGVDVMEVGFPVSSPGDFESV |

| | |
|---|---|
| 614 | QTIARQVKNSRVCALARCVEKDIDVAAESLKVAEEAFRIATFIATSPMHIATKLRSTLD |
| 1409 | QTIARQVKNSRVCALARCVEKDIDVAAESLKVAEEAFRIATFIATSPMHIATKLRSTLD |
| 1414 | QTIARTIKNSRVCGLARCVEKDIDVAAESLKVAEEAFRIATFIATSPMHIATKLRSTLD |

| | |
|---|---|
| 614 | EVIERAIYMVKRARNYTDDVEFGCEDAGRTPIADLARVVEAAINAGATTIGIADTVGY |
| 1409 | EVIERAVYMVKRARNYTDDVEFGCEDAGRTPITDLARVVEAAINAGAKTIGIADTVGY |
| 1414 | EVIERAVYMVKRARNYTDDVEFGCEDAGRTPIDDLARVVEAAINAGAKTIGIADTVGY |

| | |
|---|---|
| 614 | TMPFEFAGIISGLYERVPNIDKAIISVHTHDDLGLAVGNSLAAVHAGARQVEGAMNGI |
| 1409 | TMPFEFGAIISGLYERVPNIDKAIISVHTHDDLGLGVGNALAAVHAGARQVEGAMNGI |
| 1414 | TMPFEFSNIITGLYERVPNIDKAIISVHTHDDLGLAVGNAIAAVHAGARQVEGAMNGI |

| | |
|---|---|
| 614 | GERAGNCSLEEVIMAIKVRKDILNVHTAINHQEIWRTSQLVSQICNMPIPANKAIVGS |
| 1409 | GERAGNCSLEEVIMAIKVRKDILNVQTRINHQEIWRTSQLVSQICNMPIPANKAIVGS |
| 1414 | GERAGNCSLEEVIMAIKVRKDIMNVHTRINHNEIWRTSQTVSQICNMPIPANKAIVGT |

| | |
|---|---|
| 614 | GAFAHSSGIHQDGVLKNRENYEIMTPESIGLNQIQLNLTSRSGRAAVKHRMDEMGYKE |
| 1409 | GAFAHSSGIHQDGVLKNRENYEIMTPESIGLNQVQLNLTSRSGRAAVKHRMDEMGYKE |
| 1414 | GAFAHSSGIHQDGVLKNRENYEIMTPESIGLNQVQLNLTSRSGRAAVKHRMEEMGYKD |

| | |
|---|---|
| 614 | SEYNLDNLYDAFLKLADKKGQVFDYDLEALA |
| 1409 | NEYSLDNLYDAFLKLADKKGQVFDYDLEALA |
| 1414 | SDYNMDCLYDAFLKLADKKGQVFDYDLEALA |

SEQUENCE LISTING

<160> NUMBER OF SEQ ID NOS: 8

<210> SEQ ID NO 1
<211> LENGTH: 523
<212> TYPE: PRT
<213> ORGANISM: Citrobacter freundii

<400> SEQUENCE: 1

Met Ser Gln Gln Val Ile Ile Phe Asp Thr Thr Leu Arg Asp Gly Glu
1               5                   10                  15

Gln Ala Leu Gln Ala Ser Leu Ser Val Lys Glu Lys Leu Gln Ile Ala
            20                  25                  30

Leu Ala Leu Glu Arg Met Gly Val Asp Val Met Glu Val Gly Phe Pro
        35                  40                  45

Val Ser Ser Pro Gly Asp Phe Glu Ser Val Gln Thr Ile Ala Arg Gln
    50                  55                  60

Val Lys Asn Ser Arg Val Cys Ala Leu Ala Arg Cys Val Glu Lys Asp
65                  70                  75                  80

Ile Asp Val Ala Ala Glu Ser Leu Lys Val Ala Glu Ala Phe Arg Ile
                85                  90                  95

His Thr Phe Ile Ala Thr Ser Pro Met His Ile Ala Thr Lys Leu Arg
            100                 105                 110

Ser Thr Leu Asp Glu Val Ile Glu Arg Ala Val Tyr Met Val Lys Arg
        115                 120                 125

Ala Arg Asn Tyr Thr Asp Asp Val Glu Phe Ser Cys Glu Asp Ala Gly
    130                 135                 140

Arg Thr Pro Ile Thr Asp Leu Ala Arg Val Val Glu Ala Ala Ile Asn
145                 150                 155                 160

Ala Gly Ala Lys Thr Ile Asn Ile Pro Asp Thr Val Gly Tyr Thr Met
                165                 170                 175

Pro Phe Glu Phe Gly Ala Ile Ile Ser Gly Leu Tyr Glu Arg Val Pro

-continued

```
                180                 185                 190
Asn Ile Asp Lys Ala Ile Ile Ser Val His Thr His Asp Leu Gly
            195                 200                 205

Leu Gly Val Gly Asn Ala Leu Ala Ala Val His Ala Gly Ala Arg Gln
        210                 215                 220

Val Glu Gly Ala Met Asn Gly Ile Gly Glu Arg Ala Gly Asn Cys Ser
225                 230                 235                 240

Leu Glu Glu Val Ile Met Ala Ile Lys Val Arg Lys Asp Ile Leu Asn
                245                 250                 255

Val Gln Thr Arg Ile Asn His Gln Glu Ile Trp Arg Thr Ser Gln Leu
            260                 265                 270

Val Ser Gln Ile Cys Asn Met Pro Ile Pro Ala Asn Lys Ala Ile Val
        275                 280                 285

Gly Ser Gly Ala Phe Ala His Ser Ser Gly Ile His Gln Asp Gly Val
        290                 295                 300

Leu Lys Asn Arg Glu Asn Tyr Glu Ile Met Thr Pro Glu Ser Ile Gly
305                 310                 315                 320

Leu Asn Gln Val Gln Leu Asn Leu Thr Ser Arg Ser Gly Arg Ala Ala
                325                 330                 335

Val Lys His Arg Met Asp Glu Met Gly Tyr Lys Glu Asn Glu Tyr Ser
            340                 345                 350

Leu Asp Asn Leu Tyr Asp Ala Phe Leu Lys Leu Ala Asp Lys Lys Gly
        355                 360                 365

Gln Val Phe Asp Tyr Asp Leu Glu Ala Leu Ala Phe Ile Asn Lys Gln
        370                 375                 380

Gln Glu Glu Pro Glu His Phe Arg Leu Asp Tyr Phe Ser Val Gln Ser
385                 390                 395                 400

Gly Ser Asn Asp Ile Ala Thr Ala Ser Val Lys Leu Ala Cys Gly Glu
                405                 410                 415

Glu Val Lys Ala Glu Ala Ala Asn Gly Asn Gly Pro Val Asp Ala Ile
            420                 425                 430

Tyr Gln Ala Ile Asn Arg Val Thr Glu Tyr Asn Ile Glu Leu Val Lys
        435                 440                 445

Tyr Ser Leu Thr Ala Lys Gly His Gly Lys Asp Ala Leu Gly Gln Val
        450                 455                 460

Asp Ile Val Ala Asn Tyr Asn Gly Arg Arg Phe His Gly Val Gly Leu
465                 470                 475                 480

Ala Thr Asp Ile Val Glu Ser Ser Ala Lys Ala Met Val His Val Leu
                485                 490                 495

Asn Asn Ile Trp Arg Ala Glu Glu Val Glu Lys Glu Leu Gln Arg Lys
            500                 505                 510

Ala Gln Asn Asn Glu Asn Asn Lys Glu Thr Val
        515                 520
```

<210> SEQ ID NO 2
<211> LENGTH: 523
<212> TYPE: PRT
<213> ORGANISM: Enterobacter cloacae

<400> SEQUENCE: 2

```
Met Ser Gln Gln Val Ile Ile Phe Asp Thr Thr Leu Arg Asp Gly Glu
1               5                   10                  15

Gln Ala Leu Gln Ala Ser Leu Ser Val Lys Glu Lys Leu Gln Ile Ala
            20                  25                  30
```

-continued

```
Leu Ala Leu Glu Arg Met Gly Val Asp Val Met Glu Val Gly Phe Pro
         35                  40                  45

Val Ser Ser Pro Gly Asp Phe Glu Ser Val Gln Thr Ile Ala Arg Thr
 50                  55                  60

Ile Lys Asn Ser Arg Val Cys Gly Leu Ala Arg Cys Val Glu Lys Asp
 65                  70                  75                  80

Ile Asp Val Ala Ala Glu Ser Leu Lys Val Ala Glu Ala Phe Arg Ile
                 85                  90                  95

His Thr Phe Ile Ala Thr Ser Pro Met His Ile Ala Thr Lys Leu Arg
                100                 105                 110

Ser Thr Leu Asp Glu Val Ile Glu Arg Ala Val Tyr Met Val Lys Arg
                115                 120                 125

Ala Arg Asn Tyr Thr Asp Asp Val Glu Phe Ser Cys Glu Asp Ala Gly
130                 135                 140

Arg Thr Pro Ile Asp Asp Leu Ala Arg Val Val Glu Ala Ala Ile Asn
145                 150                 155                 160

Ala Gly Ala Lys Thr Ile Asn Ile Pro Asp Thr Val Gly Tyr Thr Met
                165                 170                 175

Pro Phe Glu Phe Ser Asn Ile Ile Thr Gly Leu Tyr Glu Arg Val Pro
                180                 185                 190

Asn Ile Asp Lys Ala Ile Ile Ser Val His Thr His Asp Asp Leu Gly
                195                 200                 205

Leu Ala Val Gly Asn Ala Ile Ala Ala Val His Ala Gly Ala Arg Gln
                210                 215                 220

Val Glu Gly Ala Met Asn Gly Ile Gly Glu Arg Ala Gly Asn Cys Ser
225                 230                 235                 240

Leu Glu Glu Val Ile Met Ala Ile Lys Val Arg Lys Asp Ile Met Asn
                245                 250                 255

Val His Thr Arg Ile Asn His Asn Glu Ile Trp Arg Thr Ser Gln Thr
                260                 265                 270

Val Ser Gln Ile Cys Asn Met Pro Ile Pro Ala Asn Lys Ala Ile Val
                275                 280                 285

Gly Thr Gly Ala Phe Ala His Ser Ser Gly Ile His Gln Asp Gly Val
290                 295                 300

Leu Lys Asn Arg Glu Asn Tyr Glu Ile Met Thr Pro Glu Ser Ile Gly
305                 310                 315                 320

Leu Asn Gln Val Gln Leu Asn Leu Thr Ser Arg Ser Gly Arg Ala Ala
                325                 330                 335

Val Lys His Arg Met Glu Glu Met Gly Tyr Lys Asp Ser Asp Tyr Asn
                340                 345                 350

Met Asp Gln Leu Tyr Asp Ala Phe Leu Lys Leu Ala Asp Lys Lys Gly
                355                 360                 365

Gln Val Phe Asp Tyr Asp Leu Glu Ala Leu Ala Phe Ile Asn Lys Gln
370                 375                 380

Gln Glu Glu Pro Glu His Phe Arg Leu Asp Tyr Phe Ser Val Gln Ser
385                 390                 395                 400

Gly Ser Ser Asp Ile Ala Thr Ala Ser Ile Lys Leu Ala Cys Gly Asp
                405                 410                 415

Glu Ile Lys Ala Glu Ala Asn Gly Asn Gly Pro Val Asp Ala Ile
                420                 425                 430

Tyr Gln Ala Ile Asn Arg Val Thr Glu Tyr Asp Val Glu Leu Val Lys
                435                 440                 445

Tyr Asp Leu Thr Ala Lys Gly His Gly Lys Asp Ala Leu Gly Gln Val
```

```
            450                 455                 460
Asp Ile Val Val Asn Tyr Asn Gly Arg Arg Phe His Gly Val Gly Leu
465                 470                 475                 480

Ala Thr Asp Ile Val Glu Ser Ser Ala Lys Ala Met Val His Val Leu
                485                 490                 495

Asn Asn Ile Trp Arg Ala Ala Glu Val Glu Lys Glu Leu Gln Arg Lys
                500                 505                 510

Ala Gln Asn Lys Glu Asn Asn Lys Glu Thr Val
                515                 520

<210> SEQ ID NO 3
<211> LENGTH: 523
<212> TYPE: PRT
<213> ORGANISM: Artificial Sequence
<220> FEATURE:
<223> OTHER INFORMATION: Synthesized - Modified C. fruendii
      isopropylmalate synthase (H97A S139G N167G P169A G181A A182G G210A
      A214S G462D)

<400> SEQUENCE: 3

Met Ser Gln Gln Val Ile Ile Phe Asp Thr Thr Leu Arg Asp Gly Glu
1               5                   10                  15

Gln Ala Leu Gln Ala Ser Leu Ser Val Lys Glu Lys Leu Gln Ile Ala
                20                  25                  30

Leu Ala Leu Glu Arg Met Gly Val Asp Val Met Glu Val Gly Phe Pro
            35                  40                  45

Val Ser Ser Pro Gly Asp Phe Glu Ser Val Gln Thr Ile Ala Arg Gln
50                  55                  60

Val Lys Asn Ser Arg Val Cys Ala Leu Ala Arg Cys Val Glu Lys Asp
65                  70                  75                  80

Ile Asp Val Ala Ala Glu Ser Leu Lys Val Ala Glu Ala Phe Arg Ile
                85                  90                  95

Ala Thr Phe Ile Ala Thr Ser Pro Met His Ile Ala Thr Lys Leu Arg
            100                 105                 110

Ser Thr Leu Asp Glu Val Ile Glu Arg Ala Val Tyr Met Val Lys Arg
        115                 120                 125

Ala Arg Asn Tyr Thr Asp Asp Val Glu Phe Gly Cys Glu Asp Ala Gly
130                 135                 140

Arg Thr Pro Ile Thr Asp Leu Ala Arg Val Val Glu Ala Ala Ile Asn
145                 150                 155                 160

Ala Gly Ala Lys Thr Ile Gly Ile Ala Asp Thr Val Gly Tyr Thr Met
                165                 170                 175

Pro Phe Glu Phe Ala Gly Ile Ile Ser Gly Leu Tyr Glu Arg Val Pro
            180                 185                 190

Asn Ile Asp Lys Ala Ile Ile Ser Val His Thr His Asp Asp Leu Gly
        195                 200                 205

Leu Ala Val Gly Asn Ser Leu Ala Ala Val His Ala Gly Ala Arg Gln
210                 215                 220

Val Glu Gly Ala Met Asn Gly Ile Gly Glu Arg Ala Gly Asn Cys Ser
225                 230                 235                 240

Leu Glu Glu Val Ile Met Ala Ile Lys Val Arg Lys Asp Ile Leu Asn
                245                 250                 255

Val Gln Thr Arg Ile Asn His Gln Glu Ile Trp Arg Thr Ser Gln Leu
            260                 265                 270

Val Ser Gln Ile Cys Asn Met Pro Ile Pro Ala Asn Lys Ala Ile Val
        275                 280                 285
```

```
Gly Ser Gly Ala Phe Ala His Ser Ser Gly Ile His Gln Asp Gly Val
            290                 295                 300

Leu Lys Asn Arg Glu Asn Tyr Glu Ile Met Thr Pro Glu Ser Ile Gly
305                 310                 315                 320

Leu Asn Gln Val Gln Leu Asn Leu Thr Ser Arg Ser Gly Arg Ala Ala
                325                 330                 335

Val Lys His Arg Met Asp Glu Met Gly Tyr Lys Glu Asn Glu Tyr Ser
            340                 345                 350

Leu Asp Asn Leu Tyr Asp Ala Phe Leu Lys Leu Ala Asp Lys Lys Gly
                355                 360                 365

Gln Val Phe Asp Tyr Asp Leu Glu Ala Leu Ala Phe Ile Asn Lys Gln
370                 375                 380

Gln Glu Glu Pro Glu His Phe Arg Leu Asp Tyr Phe Ser Val Gln Ser
385                 390                 395                 400

Gly Ser Asn Asp Ile Ala Thr Ala Ser Val Lys Leu Ala Cys Gly Glu
                405                 410                 415

Glu Val Lys Ala Glu Ala Ala Asn Gly Asn Gly Pro Val Asp Ala Ile
            420                 425                 430

Tyr Gln Ala Ile Asn Arg Val Thr Glu Tyr Asn Ile Glu Leu Val Lys
                435                 440                 445

Tyr Ser Leu Thr Ala Lys Gly His Gly Lys Asp Ala Leu Asp Gln Val
450                 455                 460

Asp Ile Val Ala Asn Tyr Asn Gly Arg Arg Phe His Gly Val Gly Leu
465                 470                 475                 480

Ala Thr Asp Ile Val Glu Ser Ser Ala Lys Ala Met Val His Val Leu
                485                 490                 495

Asn Asn Ile Trp Arg Ala Glu Val Glu Lys Glu Leu Gln Arg Lys
            500                 505                 510

Ala Gln Asn Asn Glu Asn Asn Lys Glu Thr Val
        515                 520

<210> SEQ ID NO 4
<211> LENGTH: 523
<212> TYPE: PRT
<213> ORGANISM: Artificial Sequence
<220> FEATURE:
<223> OTHER INFORMATION: Synthesized - Modified C. freundii
      isopropylmalate (H97A S139G N167G P169A G181A A182G G210A A214S
      Q258H R260A G462D)

<400> SEQUENCE: 4

Met Ser Gln Gln Val Ile Ile Phe Asp Thr Thr Leu Arg Asp Gly Glu
1               5                   10                  15

Gln Ala Leu Gln Ala Ser Leu Ser Val Lys Glu Lys Leu Gln Ile Ala
            20                  25                  30

Leu Ala Leu Glu Arg Met Gly Val Asp Val Met Glu Val Gly Phe Pro
        35                  40                  45

Val Ser Ser Pro Gly Asp Phe Glu Ser Val Gln Thr Ile Ala Arg Gln
50                  55                  60

Val Lys Asn Ser Arg Val Cys Ala Leu Ala Arg Cys Val Glu Lys Asp
65                  70                  75                  80

Ile Asp Val Ala Ala Glu Ser Leu Lys Val Ala Glu Ala Phe Arg Ile
                85                  90                  95

Ala Thr Phe Ile Ala Thr Ser Pro Met His Ile Ala Thr Lys Leu Arg
            100                 105                 110
```

```
Ser Thr Leu Asp Glu Val Ile Glu Arg Ala Val Tyr Met Val Lys Arg
            115                 120                 125

Ala Arg Asn Tyr Thr Asp Asp Val Glu Phe Gly Cys Glu Asp Ala Gly
130                 135                 140

Arg Thr Pro Ile Thr Asp Leu Ala Arg Val Val Glu Ala Ala Ile Asn
145                 150                 155                 160

Ala Gly Ala Lys Thr Ile Gly Ile Ala Asp Thr Val Gly Tyr Thr Met
                165                 170                 175

Pro Phe Glu Phe Ala Gly Ile Ile Ser Gly Leu Tyr Glu Arg Val Pro
                180                 185                 190

Asn Ile Asp Lys Ala Ile Ser Val His Thr His Asp Asp Leu Gly
            195                 200                 205

Leu Ala Val Gly Asn Ser Leu Ala Ala Val His Ala Gly Ala Arg Gln
            210                 215                 220

Val Glu Gly Ala Met Asn Gly Ile Gly Glu Arg Ala Gly Asn Cys Ser
225                 230                 235                 240

Leu Glu Glu Val Ile Met Ala Ile Lys Val Arg Lys Asp Ile Leu Asn
                245                 250                 255

Val His Thr Ala Ile Asn His Gln Glu Ile Trp Arg Thr Ser Gln Leu
            260                 265                 270

Val Ser Gln Ile Cys Asn Met Pro Ile Pro Ala Asn Lys Ala Ile Val
            275                 280                 285

Gly Ser Gly Ala Phe Ala His Ser Ser Gly Ile His Gln Asp Gly Val
            290                 295                 300

Leu Lys Asn Arg Glu Asn Tyr Glu Ile Met Thr Pro Glu Ser Ile Gly
305                 310                 315                 320

Leu Asn Gln Val Gln Leu Asn Leu Thr Ser Arg Ser Gly Arg Ala Ala
                325                 330                 335

Val Lys His Arg Met Asp Glu Met Gly Tyr Lys Glu Asn Glu Tyr Ser
            340                 345                 350

Leu Asp Asn Leu Tyr Asp Ala Phe Leu Lys Leu Ala Asp Lys Lys Gly
            355                 360                 365

Gln Val Phe Asp Tyr Asp Leu Glu Ala Leu Ala Phe Ile Asn Lys Gln
            370                 375                 380

Gln Glu Glu Pro Glu His Phe Arg Leu Asp Tyr Phe Ser Val Gln Ser
385                 390                 395                 400

Gly Ser Asn Asp Ile Ala Thr Ala Ser Val Lys Leu Ala Cys Gly Glu
                405                 410                 415

Glu Val Lys Ala Glu Ala Ala Asn Gly Asn Gly Pro Val Asp Ala Ile
            420                 425                 430

Tyr Gln Ala Ile Asn Arg Val Thr Glu Tyr Asn Ile Glu Leu Val Lys
            435                 440                 445

Tyr Ser Leu Thr Ala Lys Gly His Gly Lys Asp Ala Leu Asp Gln Val
450                 455                 460

Asp Ile Val Ala Asn Tyr Asn Gly Arg Arg Phe His Gly Val Gly Leu
465                 470                 475                 480

Ala Thr Asp Ile Val Glu Ser Ser Ala Lys Ala Met Val His Val Leu
                485                 490                 495

Asn Asn Ile Trp Arg Ala Glu Glu Val Glu Lys Glu Leu Gln Arg Lys
            500                 505                 510

Ala Gln Asn Asn Glu Asn Asn Lys Glu Thr Val
            515                 520
```

<210> SEQ ID NO 5
<211> LENGTH: 523
<212> TYPE: PRT
<213> ORGANISM: Artificial Sequence
<220> FEATURE:
<223> OTHER INFORMATION: Synthesized - Modified E. cloacae
      isopropylmalate synthase (H97A S139G N167G P169A R260A N264Q
      G462D)

<400> SEQUENCE: 5

```
Met Ser Gln Gln Val Ile Ile Phe Asp Thr Thr Leu Arg Asp Gly Glu
1               5                   10                  15

Gln Ala Leu Gln Ala Ser Leu Ser Val Lys Glu Lys Leu Gln Ile Ala
            20                  25                  30

Leu Ala Leu Glu Arg Met Gly Val Asp Val Met Glu Val Gly Phe Pro
        35                  40                  45

Val Ser Ser Pro Gly Asp Phe Glu Ser Val Gln Thr Ile Ala Arg Thr
    50                  55                  60

Ile Lys Asn Ser Arg Val Cys Gly Leu Ala Arg Cys Val Glu Lys Asp
65                  70                  75                  80

Ile Asp Val Ala Ala Glu Ser Leu Lys Val Ala Glu Ala Phe Arg Ile
                85                  90                  95

Ala Thr Phe Ile Ala Thr Ser Pro Met His Ile Ala Thr Lys Leu Arg
            100                 105                 110

Ser Thr Leu Asp Glu Val Ile Glu Arg Ala Val Tyr Met Val Lys Arg
        115                 120                 125

Ala Arg Asn Tyr Thr Asp Asp Val Glu Phe Gly Cys Glu Asp Ala Gly
    130                 135                 140

Arg Thr Pro Ile Asp Asp Leu Ala Arg Val Val Glu Ala Ala Ile Asn
145                 150                 155                 160

Ala Gly Ala Lys Thr Ile Gly Ile Ala Asp Thr Val Gly Tyr Thr Met
                165                 170                 175

Pro Phe Glu Phe Ser Asn Ile Ile Thr Gly Leu Tyr Glu Arg Val Pro
            180                 185                 190

Asn Ile Asp Lys Ala Ile Ile Ser Val His Thr His Asp Asp Leu Gly
        195                 200                 205

Leu Ala Val Gly Asn Ala Ile Ala Ala Val His Ala Gly Ala Arg Gln
    210                 215                 220

Val Glu Gly Ala Met Asn Gly Ile Gly Glu Arg Ala Gly Asn Cys Ser
225                 230                 235                 240

Leu Glu Glu Val Ile Met Ala Ile Lys Val Arg Lys Asp Ile Met Asn
                245                 250                 255

Val His Thr Ala Ile Asn His Gln Glu Ile Trp Arg Thr Ser Gln Thr
            260                 265                 270

Val Ser Gln Ile Cys Asn Met Pro Ile Pro Ala Asn Lys Ala Ile Val
    275                 280                 285

Gly Thr Gly Ala Phe Ala His Ser Ser Gly Ile His Gln Asp Gly Val
290                 295                 300

Leu Lys Asn Arg Glu Asn Tyr Glu Ile Met Thr Pro Glu Ser Ile Gly
305                 310                 315                 320

Leu Asn Gln Val Gln Leu Asn Leu Thr Ser Arg Ser Gly Arg Ala Ala
                325                 330                 335

Val Lys His Arg Met Glu Glu Met Gly Tyr Lys Asp Ser Asp Tyr Asn
            340                 345                 350

Met Asp Gln Leu Tyr Asp Ala Phe Leu Lys Leu Ala Asp Lys Lys Gly
    355                 360                 365
```

```
Gln Val Phe Asp Tyr Asp Leu Glu Ala Leu Ala Phe Ile Asn Lys Gln
    370                 375                 380

Gln Glu Glu Pro Glu His Phe Arg Leu Asp Tyr Phe Ser Val Gln Ser
385                 390                 395                 400

Gly Ser Ser Asp Ile Ala Thr Ala Ser Ile Lys Leu Ala Cys Gly Asp
            405                 410                 415

Glu Ile Lys Ala Glu Ala Asn Gly Asn Gly Pro Val Asp Ala Ile
            420                 425                 430

Tyr Gln Ala Ile Asn Arg Val Thr Glu Tyr Asp Val Glu Leu Val Lys
            435                 440                 445

Tyr Asp Leu Thr Ala Lys Gly His Gly Lys Asp Ala Leu Asp Gln Val
450                 455                 460

Asp Ile Val Val Asn Tyr Asn Gly Arg Arg Phe His Gly Val Gly Leu
465                 470                 475                 480

Ala Thr Asp Ile Val Glu Ser Ser Ala Lys Ala Met Val His Val Leu
            485                 490                 495

Asn Asn Ile Trp Arg Ala Ala Glu Val Glu Lys Glu Leu Gln Arg Lys
            500                 505                 510

Ala Gln Asn Lys Glu Asn Asn Lys Glu Thr Val
            515                 520
```

<210> SEQ ID NO 6
<211> LENGTH: 523
<212> TYPE: PRT
<213> ORGANISM: Artificial Sequence
<220> FEATURE:
<223> OTHER INFORMATION: Synthesized - Modified E. cloacae
      isopropylmalate synthase (H97A S139G N167G P169A R260A N264Q G462D
      M255L)

<400> SEQUENCE: 6

```
Met Ser Gln Gln Val Ile Ile Phe Asp Thr Thr Leu Arg Asp Gly Glu
1               5                   10                  15

Gln Ala Leu Gln Ala Ser Leu Ser Val Lys Glu Lys Leu Gln Ile Ala
            20                  25                  30

Leu Ala Leu Glu Arg Met Gly Val Asp Val Met Glu Val Gly Phe Pro
        35                  40                  45

Val Ser Ser Pro Gly Asp Phe Glu Ser Val Gln Thr Ile Ala Arg Thr
50                  55                  60

Ile Lys Asn Ser Arg Val Cys Gly Leu Ala Arg Cys Val Glu Lys Asp
65                  70                  75                  80

Ile Asp Val Ala Ala Glu Ser Leu Lys Val Ala Glu Ala Phe Arg Ile
            85                  90                  95

Ala Thr Phe Ile Ala Thr Ser Pro Met His Ile Ala Thr Lys Leu Arg
                100                 105                 110

Ser Thr Leu Asp Glu Val Ile Glu Arg Ala Val Tyr Met Val Lys Arg
        115                 120                 125

Ala Arg Asn Tyr Thr Asp Asp Val Glu Phe Gly Cys Glu Asp Ala Gly
    130                 135                 140

Arg Thr Pro Ile Asp Asp Leu Ala Arg Val Val Glu Ala Ala Ile Asn
145                 150                 155                 160

Ala Gly Ala Lys Thr Ile Gly Ile Ala Asp Thr Val Gly Tyr Thr Met
            165                 170                 175

Pro Phe Glu Phe Ser Asn Ile Ile Thr Gly Leu Tyr Glu Arg Val Pro
                180                 185                 190
```

```
Asn Ile Asp Lys Ala Ile Ile Ser Val His Thr His Asp Leu Gly
            195                 200                 205

Leu Ala Val Gly Asn Ala Ile Ala Ala Val His Ala Gly Ala Arg Gln
        210                 215                 220

Val Glu Gly Ala Met Asn Gly Ile Gly Glu Arg Ala Gly Asn Cys Ser
225                 230                 235                 240

Leu Glu Glu Val Ile Met Ala Ile Lys Val Arg Lys Asp Ile Leu Asn
                245                 250                 255

Val His Thr Ala Ile Asn His Gln Glu Ile Trp Arg Thr Ser Gln Thr
            260                 265                 270

Val Ser Gln Ile Cys Asn Met Pro Ile Pro Ala Asn Lys Ala Ile Val
        275                 280                 285

Gly Thr Gly Ala Phe Ala His Ser Ser Gly Ile His Gln Asp Gly Val
290                 295                 300

Leu Lys Asn Arg Glu Asn Tyr Glu Ile Met Thr Pro Glu Ser Ile Gly
305                 310                 315                 320

Leu Asn Gln Val Gln Leu Asn Leu Thr Ser Arg Ser Gly Arg Ala Ala
                325                 330                 335

Val Lys His Arg Met Glu Glu Met Gly Tyr Lys Asp Ser Asp Tyr Asn
            340                 345                 350

Met Asp Gln Leu Tyr Asp Ala Phe Leu Lys Leu Ala Asp Lys Lys Gly
        355                 360                 365

Gln Val Phe Asp Tyr Asp Leu Glu Ala Leu Ala Phe Ile Asn Lys Gln
        370                 375                 380

Gln Glu Glu Pro Glu His Phe Arg Leu Asp Tyr Phe Ser Val Gln Ser
385                 390                 395                 400

Gly Ser Ser Asp Ile Ala Thr Ala Ser Ile Lys Leu Ala Cys Gly Asp
                405                 410                 415

Glu Ile Lys Ala Glu Ala Asn Gly Asn Gly Pro Val Asp Ala Ile
            420                 425                 430

Tyr Gln Ala Ile Asn Arg Val Thr Glu Tyr Asp Val Glu Leu Val Lys
        435                 440                 445

Tyr Asp Leu Thr Ala Lys Gly His Gly Lys Asp Ala Leu Asp Gln Val
450                 455                 460

Asp Ile Val Val Asn Tyr Asn Gly Arg Arg Phe His Gly Val Gly Leu
465                 470                 475                 480

Ala Thr Asp Ile Val Glu Ser Ser Ala Lys Ala Met Val His Val Leu
                485                 490                 495

Asn Asn Ile Trp Arg Ala Ala Gly Val Glu Lys Glu Leu Gln Arg Lys
            500                 505                 510

Ala Gln Asn Lys Glu Asn Asn Lys Glu Thr Val
        515                 520

<210> SEQ ID NO 7
<211> LENGTH: 523
<212> TYPE: PRT
<213> ORGANISM: Artificial Sequence
<220> FEATURE:
<223> OTHER INFORMATION: Synthesized - Modified E. cloacase
      isopropylmalate synthase (H97A S139G N167G P169A D348E D350E M353L
      Q355N G462D)

<400> SEQUENCE: 7

Met Ser Gln Gln Val Ile Ile Phe Asp Thr Thr Leu Arg Asp Gly Glu
1               5                   10                  15

Gln Ala Leu Gln Ala Ser Leu Ser Val Lys Glu Lys Leu Gln Ile Ala
```

```
            20                  25                  30
Leu Ala Leu Glu Arg Met Gly Val Asp Val Met Glu Val Gly Phe Pro
        35                  40                  45
Val Ser Ser Pro Gly Asp Phe Glu Ser Val Gln Thr Ile Ala Arg Thr
    50                  55                  60
Ile Lys Asn Ser Arg Val Cys Gly Leu Ala Arg Cys Val Glu Lys Asp
65                  70                  75                  80
Ile Asp Val Ala Ala Glu Ser Leu Lys Val Ala Glu Ala Phe Arg Ile
                85                  90                  95
Ala Thr Phe Ile Ala Thr Ser Pro Met His Ile Ala Thr Lys Leu Arg
            100                 105                 110
Ser Thr Leu Asp Glu Val Ile Glu Arg Ala Val Tyr Met Val Lys Arg
        115                 120                 125
Ala Arg Asn Tyr Thr Asp Val Glu Phe Gly Cys Glu Asp Ala Gly
    130                 135                 140
Arg Thr Pro Ile Asp Asp Leu Ala Arg Val Glu Ala Ala Ile Asn
145                 150                 155                 160
Ala Gly Ala Lys Thr Ile Gly Ile Ala Asp Thr Val Gly Tyr Thr Met
                165                 170                 175
Pro Phe Glu Phe Ser Asn Ile Ile Thr Gly Leu Tyr Glu Arg Val Pro
            180                 185                 190
Asn Ile Asp Lys Ala Ile Ile Ser Val His Thr His Asp Asp Leu Gly
        195                 200                 205
Leu Ala Val Gly Asn Ala Ile Ala Ala Val His Ala Gly Ala Arg Gln
    210                 215                 220
Val Glu Gly Ala Met Asn Gly Ile Gly Glu Arg Ala Gly Asn Cys Ser
225                 230                 235                 240
Leu Glu Glu Val Ile Met Ala Ile Lys Val Arg Lys Asp Ile Met Asn
                245                 250                 255
Val His Thr Arg Ile Asn His Asn Glu Ile Trp Arg Thr Ser Gln Thr
            260                 265                 270
Val Ser Gln Ile Cys Asn Met Pro Ile Pro Ala Asn Lys Ala Ile Val
        275                 280                 285
Gly Thr Gly Ala Phe Ala His Ser Ser Gly Ile His Gln Asp Gly Val
    290                 295                 300
Leu Lys Asn Arg Glu Asn Tyr Glu Ile Met Thr Pro Glu Ser Ile Gly
305                 310                 315                 320
Leu Asn Gln Val Gln Leu Asn Leu Thr Ser Arg Ser Gly Arg Ala Ala
                325                 330                 335
Val Lys His Arg Met Glu Glu Met Gly Tyr Lys Glu Ser Glu Tyr Asn
            340                 345                 350
Leu Asp Asn Leu Tyr Asp Ala Phe Leu Lys Leu Ala Asp Lys Lys Gly
        355                 360                 365
Gln Val Phe Asp Tyr Asp Leu Glu Ala Leu Ala Phe Ile Asn Lys Gln
    370                 375                 380
Gln Glu Glu Pro Glu His Phe Arg Leu Asp Tyr Phe Ser Val Gln Ser
385                 390                 395                 400
Gly Ser Ser Asp Ile Ala Thr Ala Ser Ile Lys Leu Ala Cys Gly Asp
                405                 410                 415
Glu Ile Lys Ala Glu Ala Ala Asn Gly Asn Gly Pro Val Asp Ala Ile
            420                 425                 430
Tyr Gln Ala Ile Asn Arg Val Thr Glu Tyr Asp Val Glu Leu Val Lys
        435                 440                 445
```

Tyr Asp Leu Thr Ala Lys Gly His Gly Lys Asp Ala Leu Asp Gln Val
            450                 455                 460

Asp Ile Val Val Asn Tyr Asn Gly Arg Arg Phe His Gly Val Gly Leu
465                 470                 475                 480

Ala Thr Asp Ile Val Glu Ser Ser Ala Lys Ala Met Val His Val Leu
            485                 490                 495

Asn Asn Ile Trp Arg Ala Ala Glu Val Glu Lys Glu Leu Gln Arg Lys
            500                 505                 510

Ala Gln Asn Lys Glu Asn Asn Lys Glu Thr Val
            515                 520

<210> SEQ ID NO 8
<211> LENGTH: 523
<212> TYPE: PRT
<213> ORGANISM: Artificial Sequence
<220> FEATURE:
<223> OTHER INFORMATION: Synthesized - Modified E. cloacae
      isopropylmalate synthase (H97A S139G N167G P169A D348E D350E M353L
      Q355N G462D M255L R260A N264Q)

<400> SEQUENCE: 8

Met Ser Gln Gln Val Ile Ile Phe Asp Thr Thr Leu Arg Asp Gly Glu
1               5                   10                  15

Gln Ala Leu Gln Ala Ser Leu Ser Val Lys Glu Lys Leu Gln Ile Ala
            20                  25                  30

Leu Ala Leu Glu Arg Met Gly Val Asp Val Met Glu Val Gly Phe Pro
        35                  40                  45

Val Ser Ser Pro Gly Asp Phe Glu Ser Val Gln Thr Ile Ala Arg Thr
50                  55                  60

Ile Lys Asn Ser Arg Val Cys Gly Leu Ala Arg Cys Val Glu Lys Asp
65                  70                  75                  80

Ile Asp Val Ala Ala Glu Ser Leu Lys Val Ala Glu Ala Phe Arg Ile
            85                  90                  95

Ala Thr Phe Ile Ala Thr Ser Pro Met His Ile Ala Thr Lys Leu Arg
            100                 105                 110

Ser Thr Leu Asp Glu Val Ile Glu Arg Ala Val Tyr Met Val Lys Arg
            115                 120                 125

Ala Arg Asn Tyr Thr Asp Asp Val Glu Phe Gly Cys Glu Asp Ala Gly
            130                 135                 140

Arg Thr Pro Ile Asp Asp Leu Ala Arg Val Val Glu Ala Ala Ile Asn
145                 150                 155                 160

Ala Gly Ala Lys Thr Ile Gly Ile Ala Asp Thr Val Gly Tyr Thr Met
            165                 170                 175

Pro Phe Glu Phe Ser Asn Ile Ile Thr Gly Leu Tyr Glu Arg Val Pro
            180                 185                 190

Asn Ile Asp Lys Ala Ile Ile Ser Val His Thr His Asp Asp Leu Gly
            195                 200                 205

Leu Ala Val Gly Asn Ala Ile Ala Ala Val His Ala Gly Ala Arg Gln
            210                 215                 220

Val Glu Gly Ala Met Asn Gly Ile Gly Glu Arg Ala Gly Asn Cys Ser
225                 230                 235                 240

Leu Glu Glu Val Ile Met Ala Ile Lys Val Arg Lys Asp Ile Leu Asn
            245                 250                 255

Val His Thr Ala Ile Asn His Gln Glu Ile Trp Arg Thr Ser Gln Thr
            260                 265                 270

-continued

```
Val Ser Gln Ile Cys Asn Met Pro Ile Pro Ala Asn Lys Ala Ile Val
        275                 280                 285
Gly Thr Gly Ala Phe Ala His Ser Ser Gly Ile His Gln Asp Gly Val
        290                 295                 300
Leu Lys Asn Arg Glu Asn Tyr Glu Ile Met Thr Pro Glu Ser Ile Gly
305                 310                 315                 320
Leu Asn Gln Val Gln Leu Asn Leu Thr Ser Arg Ser Gly Arg Ala Ala
                325                 330                 335
Val Lys His Arg Met Glu Met Gly Tyr Lys Glu Ser Glu Tyr Asn
                340                 345                 350
Leu Asp Asn Leu Tyr Asp Ala Phe Leu Lys Leu Ala Asp Lys Lys Gly
        355                 360                 365
Gln Val Phe Asp Tyr Asp Leu Glu Ala Leu Ala Phe Ile Asn Lys Gln
        370                 375                 380
Gln Glu Glu Pro Glu His Phe Arg Leu Asp Tyr Phe Ser Val Gln Ser
385                 390                 395                 400
Gly Ser Ser Asp Ile Ala Thr Ala Ser Ile Lys Leu Ala Cys Gly Asp
                405                 410                 415
Glu Ile Lys Ala Glu Ala Ala Asn Gly Asn Gly Pro Val Asp Ala Ile
                420                 425                 430
Tyr Gln Ala Ile Asn Arg Val Thr Glu Tyr Asp Val Glu Leu Val Lys
                435                 440                 445
Tyr Asp Leu Thr Ala Lys Gly His Gly Lys Asp Ala Leu Asp Gln Val
        450                 455                 460
Asp Ile Val Val Asn Tyr Asn Gly Arg Arg Phe His Gly Val Gly Leu
465                 470                 475                 480
Ala Thr Asp Ile Val Glu Ser Ser Ala Lys Ala Met Val His Val Leu
                485                 490                 495
Asn Asn Ile Trp Arg Ala Ala Glu Val Glu Lys Glu Leu Gln Arg Lys
                500                 505                 510
Ala Gln Asn Lys Glu Asn Asn Lys Glu Thr Val
        515                 520
```

US 10,995,322 B2

PROCESSES TO PREPARE ELONGATED 2-KETOACIDS AND C5-C10 COMPOUNDS THEREFROM VIA GENETIC MODIFICATIONS TO MICROBIAL METABOLIC PATHWAYS

CROSS-REFERENCE TO RELATED APPLICATIONS

This application claims the benefit of U.S. Provisional Application Ser. No. 62/402,586, filed Sep. 30, 2016, and also U.S. Provisional Application Ser. No. 62/402,569 filed Sep. 30, 2016, both of which are hereby incorporated by reference in their entirety.

SEQUENCE LISTING

This application incorporates by reference the material in the ASCII text file "79045-WO-PCT_SequenceListing.txt" of 37,000 bytes created on Aug. 23, 2016 and filed in U.S. Provisional Application Ser. No. 62/402,586, on Sep. 30, 2016.

FIELD

The present disclosure relates to using biological enzymes to produce $C_7$-$C_{11}$ 2-ketoacids and products made therefrom. More particularly, the present disclosure relates to genetically modified isopropylmalate synthases, methods of using such genetically modified isopropylmalate synthases to convert a 2-ketoacid substrate to $C_7$-$C_{11}$ 2-ketoacids, $C_6$-$C_{10}$ aldehydes, $C_6$-$C_{10}$ alcohols, $C_6$-$C_{10}$ carboxylic acids, and $C_5$-$C_9$ alkanes, and microbial organisms including genetically modified isopropylmalate synthases.

BACKGROUND

Concerns about the future scarcity, cost, and environmental impact of obtaining and using fossil fuels have stimulated interest in the exploitation of cheap, renewable biomass as alternative sources for both fuels and chemicals made from them. As crude oil prices have risen, bio-based chemicals and industrial products have become attractive alternatives to their petroleum-derived counterparts. Fermentation processes using anaerobic microbial organisms offer a promising path for converting biomass and agricultural wastes into useful products, while at the same time remediating problems that may be encountered in disposal of low-value agricultural commodities and food processing byproducts/wastes. Some of the useful products that can be prepared from low-cost biomass feedstocks are longer chain aldehydes, alkanes, alcohols, alkenes, and carboxylic acids, including in particular $C_6$-$C_{10}$ alcohols.

$C_6$-$C_{10}$ alcohols are produced using petrochemical and natural raw material routes. The petrochemical processes are based upon ethylene oligomerization. The Ziegler process uses aluminum to mediate ethylene oligomerization at high pressure to generate tri-alkyl aluminum species which are then carefully oxidized under dry air and hydrolyzed to yield a Poisson distribution of terminal alcohols ranging from $C_2$-$C_{26}$ (even number carbon chains only). Hydroformylation of olefins produced by ethylene oligomerization processes such as the Shell Higher Olefins Process (SHOP) followed by reduction, yields alcohols with odd number carbon chain lengths. The conversion of fatty acids of natural oils such as palm kernel and coconut through the standard oleochemical transformation of hydrogenation, transesterification and reduction is also employed to make long chain alcohols with the bulk of the alcohols having carbon chains >$C_{10}$. The lack of selectivity to narrow carbon chain length distribution is a significant drawback of the current production methods. The Ziegler process also suffers from the co-production of hydrated alumina ($Al_2O_3$ [$H_2O$]$_x$). Thus, identification of better (i.e. selective to a small range of carbon chain length) and less expensive methods to produce $C_6$-$C_{10}$ alcohols, alkanes, and carboxylic acids would be of great utility. However, microorganisms often fail to produce many of the petrochemical based products at economically viable rates or yields. Metabolic engineering has been extensively employed to either to build pathways and/or to channel metabolites toward the pathway of interest. Currently, ethanol is the most common biochemical made using microorganisms. However, economically viable methods for producing $C_6$-$C_{10}$ alcohols and carboxylic acids are being actively pursued in both the biofuel and chemical industries.

The success in the production of natural amino acids by microbial fermentation has generated significant interest in utilizing the amino acid biosynthetic pathways for producing chemicals of interest, including the longer chain alcohols, alkanes, and carboxylic acids. Of particular interest are the 2-ketoacids, which are key intermediates during amino acid biosynthesis and which are amenable to different types of modifications that can be exploited for the biosynthesis of chemicals inside the cells. Three enzymes within the leucine biosynthetic pathway are involved in elongating 2-ketoacids and can operate to convert 2-ketobutyrate or 2-ketoisovalerate to a longer chain 2-ketoacids. These enzymes are generally referred to, without reference to any specific microbial organism, as isopropylmalate synthase, isopropylmalate isomerase, and isopropylmalate dehydrogenase. In *E. coli* specifically, these enzymes are referred to as LeuA (GenBank: Accession No. NC 000913.3 Gene ID: 947465), LeuB (GenBank: Accession NO. NC 000913.3 Gene ID: 944798), and LeuCD (GenBank: Accession No. NC 000913.3 Gene ID: 94576 and Gene ID: 945642), respectively. The feasibility of extending the length of 2-ketoacids inside the cell via engineering of the LeuA gene product of *E. coli* has also expanded the range of biochemicals that can be produced from 2-ketoacids. In *E. coli*, LeuABCD genes extend the length of 2-ketoacids by one carbon unit, as observed during leucine biosynthesis, in which they work together to convert 2-ketoisovalerate (a 5-carbon acid) to 2-ketoisocaproate (a 6-carbon acid). The expansion of the active site of LeuA allowed for the recursive extension of the $C_4$ ketoacid, 2-ketobutyric acid [2-ketobutyrate], to a $C_9$ 2-ketoacid, 2-ketononanoic acid [2-keto-nonanoate].

However, there is a continued need for the development and engineering of isopropylmalate synthase, isopropylmalate isomerase, and isopropylmalate dehydrogenase for a more efficient production of $C_7$-$C_{11}$ 2-ketoacids in a variety of microorganims Additionally, there is a need to produce isopropylmalate synthases, isopropylmalate isomerases, and isopropylmalate dehydrogenases with a varied catalytic efficiencies in order to better regulate the recursive extension of the $C_4$ ketoacids, such as 2-ketobutyrate or 2-ketoisovalerate, to a $C_7$-$C_{11}$ 2-ketoacid to match a microorganism's cellular metabolism with 2-ketoacid elongation.

SUMMARY

Embodiments of the present disclosure meet those needs by providing genetically modified isopropylmalate synthases, processes for preparing a $C_7$-$C_{11}$ 2-ketoacid utilizing such genetically modified isopropylmalate synthases, and microbial organisms including such modified isopropylmalate synthases. The genetically modified isopropylmalate synthases, can be used to produce bio-based chemicals and industrial products in a variety of microbial organisms, and are attractive alternatives to using fossil fuels.

According to embodiments of the present disclosure, a genetically modified isopropylmalate synthase polypeptide having isopropylmalate synthase activity is provided. The polypeptide includes an amino acid sequence with at least 80% homology to SEQ ID NO: 1 and includes the mutations H97A, S139G, N167G, P169A, G181A, A182G, G210A, A214S, and G462D.

According to other embodiments of the present disclosure, a genetically modified isopropylmalate synthase polypeptide having isopropylmalate synthase activity is provided. The polypeptide includes an amino acid sequence with at least 80% homology to SEQ ID NO: 2 and includes the mutations H97A, S139G, N167G, P169A, R260A, N264Q, and G462D.

According to additional embodiments of the present disclosure, a genetically modified isopropylmalate synthase polypeptide having isopropylmalate synthase activity is provided. The polypeptide includes an amino acid sequence with at least 80% homology to SEQ ID NO: 2 and includes the mutations H97A, S139G, N167G, P169A, D348E, D350E, M353L, Q355N, and G462D.

According to further embodiments of the present disclosure, a process for preparing a $C_7$-$C_{11}$ 2-ketoacid is provided. The process includes providing at least one of a $C_4$-$C_{10}$ 2-ketoacid substrate with (a) a genetically modified isopropylmalate synthase (IPMS) having IPMS activity, (b) a isopropylmalate isomerase having isopropylmalate isomerase activity, and (c) a isopropylmalate dehydrogenase having isopropylmalate dehydrogenase activity, under conditions that the at least one of the $C_4$-$C_{10}$ 2-ketoacid substrate is converted to the $C_7$-$C_{11}$ 2-ketoacid. The genetically modified isopropylmalate synthase having IPMS activity includes at least one of: (i) an amino acid sequence having at least 80% homology to SEQ ID NO: 1 and including the mutations H97A, S139G, N167G, P169A, G181A, A182G, G210A, A214S, and G462D; (ii) an amino acid sequence having at least 80% homology to SEQ ID NO: 2 and including the mutations H97A, S139G, N167G, P169A, R260A, N264Q, and G462D; or (iii) an amino acid sequence having at least 80% homology to SEQ ID NO: 2 and including the mutations H97A, S139G, N167G, P169A, D348E, D350E, M353L, Q355N, and G462D. The conversion of the at least one of the $C_4$-$C_{10}$ 2-ketoacid substrate to the $C_7$-$C_{11}$ 2-ketoacid occurs via one or more biochemical reactions.

In yet another embodiment, a microbial organism having a genetically modified isopropylmalate synthase (IPMS) is provided. The microbial organism includes at least one of: (i) an IPMS having an amino acid sequence with at least 80% homology to SEQ ID NO: 1 and including the mutations H97A, S139G, N167G, P169A, G181A, A182G, G210A, A214S, and G462D, the IPMS having IPMS activity; (ii) an IPMS having an amino acid sequence with at least 80% homology to SEQ ID NO: 2 and including the mutations H97A, S139G, N167G, P169A, R260A, N264Q, and G462D, the IPMS having IPMS activity; or (iii) an IPMS having an amino acid sequence with at least 80% homology to SEQ ID NO: 2 and including the mutations H97A, S139G, N167G, P169A, D348E, D350E, M353L, Q355N, and G462D, the IPMS having IPMS activity.

It is understood that both the following summary and the detailed description are exemplary and explanatory and are intended to provide further explanation of the disclosure as claimed. Neither the summary nor the description that follows is intended to define or limit the scope of the disclosure to the particular features mentioned in the summary or description.

BRIEF DESCRIPTION OF THE DRAWINGS

FIG. 1 shows the elongation of a 2-ketoacid by the recursive activities of isopropylmalate synthase, isopropylmalate isomerase, and isopropylmalate dehydrogenase (termed "the LeuABCD pathway" in *E. coli*), in 1 to 3. Following the elongation, the resulting elongated 2-ketoacid (IV) is then converted to an aldehyde (V), via the activity of a (thiamin dependent) decarboxylase in 4, and finally to an alcohol (VI) in 5, via the activity of an alcohol dehydrogenase.

FIG. 2 shows two related but different routes to produce 1-heptanol. In the first route, a Wood-Ljungdahl pathway converts synthesis gas to acetyl CoA, and another pathway then converts the acetyl CoA to pyruvate. The pyruvate is then converted to 2-ketobutyrate, and finally a LeuABCD pathway is initiated, wherein the 2-ketobutyrate is converted to $C_7$-$C_{11}$ 2-ketoacid (in this embodiment; 2-ketooctanoate). Once the elongated 2-ketoacid has been formed (the 2-ketooctanoate), a (thiamin dependent) decarboxylase converts it to a $C_6$-$C_{10}$ aldehyde (in this embodiment, heptanol), and an alcohol dehydrogenase converts it the $C_6$-$C_{10}$ aldehyde to a $C_6$-$C_{10}$ alcohol (in this embodiment, 1-heptanol). In the second route, one of the potential sugar catabolism pathways, which in this embodiment is a glycolysis or pentose phosphate pathway, converts a $C_5$ or $C_6$ sugar to pyruvate, and thereafter the same pathway sequence is followed as in the first route to reach the heptanol.

FIG. 3. Sequence alignments of amino acids 1-379 of constructs 614 (i.e., E. coil_LeuAva variant reported by Marcheschi et al. ACS Chem. Biol. 2012, 7, 689-697), 1409, and 1414. FIG. 3 depicts the amino acid substitutions between the three protein sequences, which are highlighted in grey.

DETAILED DESCRIPTION

Figure 1:
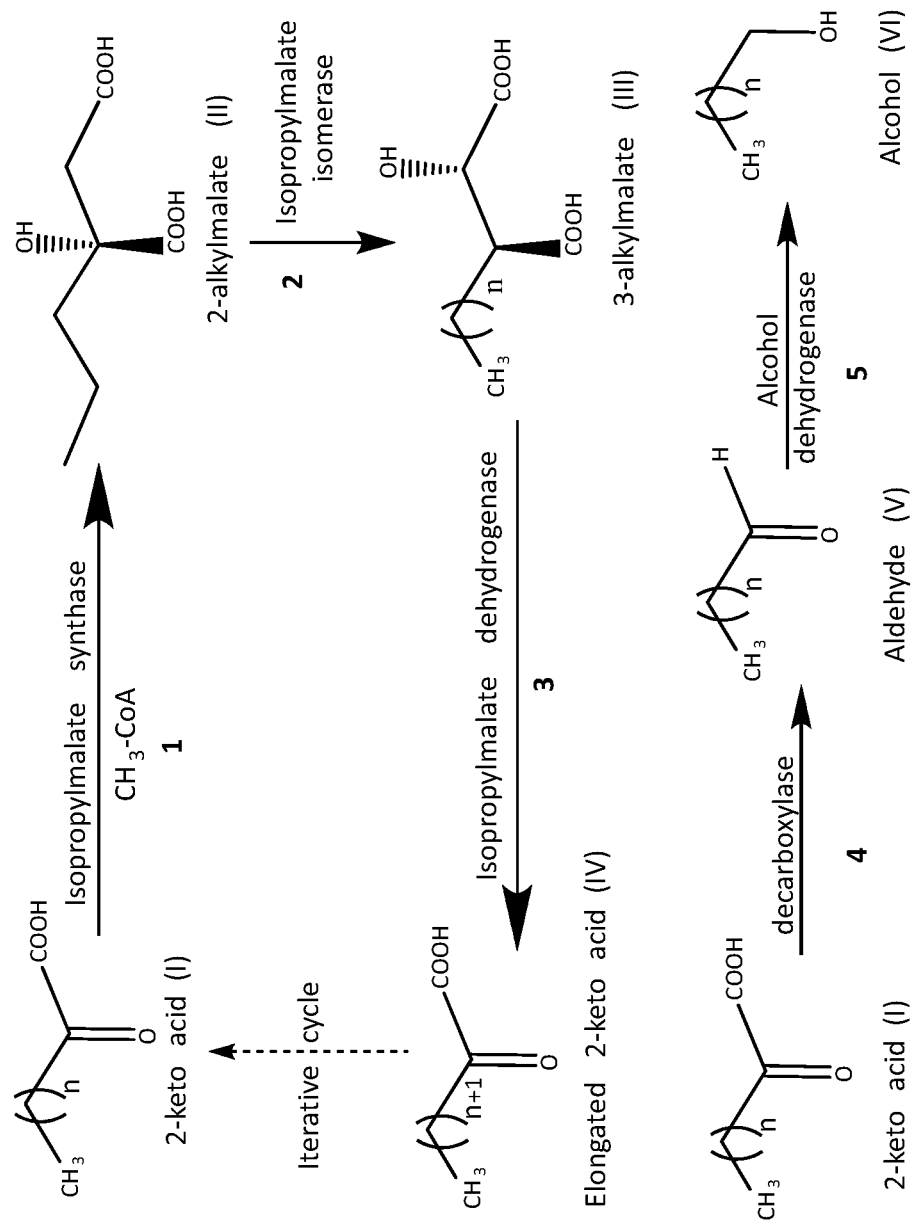
FIG. 1. Elongation of a 2-ketoacid.

Reference will now be made in detail to various embodiments of the instantly-disclosed genetically modified isopropylmalate synthases, processes for preparing a $C_7$-$C_{11}$ 2-ketoacid utilizing such genetically modified isopropylmalate synthases, and microbial organisms including such modified isopropylmalate synthases. The genetically modified isopropylmalate synthases, processes, and microbial organisms can be used to produce bio-based chemicals and industrial products, and are attractive alternatives to using fossil fuels. The instantly-disclosed genetically modified isopropylmalate synthases, processes, and microbial organisms can be particularly useful for producing longer chain alkanes, alcohols, alkenes, and carboxylic acids, both in vivo and in vitro. Additionally, the genetically modified isopropylmalate synthases are from two different species of microbial organisms and have improved and varied catalytic efficiencies at capturing and condensing acetyl coenzyme A (acetyl CoA) and longer chain 2-ketoacids, particularly 2-ketooctanoate. Thus, these isopropylmalate synthases can be utilized to better regulate the recursive extension of the $C_4$ ketoacids, such as 2-ketobutyrate or 2-ketoisovalerate, to a $C_7$-$C_{11}$ 2-ketoacid to match a microorganism's cellular metabolism with 2-ketoacid elongation.

As used herein, the singular forms "a," "an" and "the" include plural referents unless the context clearly dictates otherwise. Thus, for example, reference to "a" component includes aspects having two or more such components, unless the context clearly indicates otherwise.

In various embodiments, genetically modified isopropylmalate synthase polypeptides with isopropylmalate synthase activity are provided. The terms "polypeptide" or "protein" are used interchangeably herein. As is known in the art, polypeptides or proteins have one or more chains of amino acids that can be linked together by peptide bonds. In certain embodiments, the genetically modified isopropylmalate synthase polypeptides are purified. Embodiments of the genetically modified isopropylmalate synthases include a number of altered amino acid sequences of isopropylmalate synthases from two different species of microbial organisms: *Citrobacter freundii* and *Enterobacter cloacae*. These genetically modified isopropylmalate synthases exhibit improved activity and catalytic efficiency ($k_{cat}/K_m$) at capturing and condensing acetyl CoA and $C_6$-$C_{10}$ 2-ketoacids, particularly 2-ketooctanoate, in comparison with a previously disclosed genetically modified isopropylmalate synthase from *E. coli* (i.e., LeuA: GenBank Accession Number NC_000913.3, Gene ID 947465) with mutations H97A, S139G, N167G, P169A, and G462D in the active site of the isopropylmalate synthase. The notation for these specific genetic modifications, as well as similar notations for genetic modifications disclosed throughout the instant specification, adhere to industry standard wherein amino acid modifications are defined as the original single letter amino acid code, followed by the amino acid position, followed by the new amino acid single letter code. These previously disclosed genetic modifications to the isopropylmalate synthase from *E. coli* (i.e, LeuA) resulted in the expansion of the active site of LeuA, which allowed for the recursive extension of the $C_4$ ketoacid, 2-ketobutyric acid [2-ketobutyrate], to a $C_9$ 2-ketoacid, 2-ketononanoic acid [2-keto-nonanoate].

Surprisingly, the current investigators determined that when these same mutations from the previously disclosed genetically modified isopropylmalate synthase from *E. coli* were made in the isopropylmalate synthases from various organisms, including *Citrobacter freundii* and *Enterobacter cloacae*, there was improved substrate specificity of these isopropylmalate synthases toward longer chain 2-ketoacids, but very poor catalytic activity. However, the current investigators determined that certain specific additional mutations within the catalytic domain of the isopropylmalate synthases from *Citrobacter freundii* and *Enterobacter cloacae* resulted in the instantly-disclosed genetically modified isopropylmalate synthases with improved catalytic efficiency ($k_{cat}/K_m$) at capturing and condensing acetyl-CoA and 2-ketooctanoate. These additional mutations within the catalytic domain of the isopropylmalate synthases from *Citrobacter freundii* and *Enterobacter cloacae* also resulted in the instantly-disclosed genetically modified isopropylmalate synthases with varied catalytic efficiency (i.e., $k_{cat}/K_m$) at capturing and condensing acetyl CoA and 2-ketooctanoate, which can be advantageously utilized to match a microorganism's cellular metabolism with 2-ketoacid elongation. Thus, the instantly-disclosed genetically modified isopropylmalate synthases can be particularly useful for more efficiently producing $C_6$-$C_{10}$ aldehydes, alkanes, alcohols, and carboxylic acids, both in vivo and in vitro.

Various sites within the catalytic domain of isopropylmalate synthase from *Citrobacter freundii* and *Enterobacter cloacae* have been identified as key to obtaining the improvements. The catalytic domain of isopropylmalate synthase from these two species of microbial organisms is made up of residues 1-379. The genetic mutations within the wild type sequence of isopropylmalate synthase from *Citrobacter freundii* (Gene Accession No. KDF09799) that resulted in the improved catalytic activity include H97A, S139G, N167G, P169A, and G462D within the active site, and combinations of G181A, A182G, G210A, A214S, G462D, Q258H, and R260A within the catalytic domain. The genetic mutations within the wild type sequence of isopropylmalate synthase from *Enterobacter cloacae* (Gene Accession No. WP_014830637) that resulted in the improved catalytic activity include H97A, S139G, N167G, P169A, and G462D within the active site, and combinations of M255L, R260A, N264Q, D348E, F350E, M353L, and Q355N within the catalytic domain. SEQ ID NO: 3-4 show amino acid sequences for the variations of isopropylmalate synthase from *Citrobacter freundii* that include the various substitutions as specified. SEQ ID NO: 5-8 show amino acid sequences for the variations of isopropylmalate synthase from *Enterobacter cloacae* that include the various substitutions as specified.

In some embodiments, the genetically modified isopropylmalate synthase polypeptide having isopropylmalate synthase includes an amino acid sequence with at least 80% homology to SEQ ID NO: 1 and having the mutations H97A, S139G, N167G, P169A, G181A, A182G, G210A, A214S, and G462D. In some embodiments of the genetically modified isopropylmalate synthase polypeptide having an amino acid sequence with at least 80% homology to SEQ ID NO: 1, the polypeptide has at least 80% homology to residues 1-379 that make up the catalytic domain of SEQ ID NO: 1 (shown in FIG. 3). In some embodiments, the genetically modified isopropylmalate synthase polypeptide having isopropylmalate synthase includes an amino acid sequence with at least 90% homology to SEQ ID NO: 1 and having the mutations H97A, S139G, N167G, P169A, G181A, A182G, G210A, A214S, and G462D. In some embodiments of the genetically modified isopropylmalate synthase polypeptide having isopropylmalate synthase includes an amino acid sequence with at least 90% homology to SEQ ID NO: 1 and having the mutations H97A, S139G, N167G, P169A, G181A, A182G, G210A, A214S, and G462D, the polypeptide has at least 90% homology to residues 1-379 that make up the catalytic domain of SEQ ID NO: 1 (shown in FIG. 3). In some embodiments, the amino acid sequence of the genetically modified isopropylmalate synthase is obtained from *Citrobacter freundii*. In certain embodiments, the genetically modified isopropylmalate synthase polypeptide further includes the mutations Q258H and R260A. In certain embodiments, the polypeptide is a purified polypeptides.

According to another embodiment of the present disclosure, a genetically modified isopropylmalate synthase polypeptide having isopropylmalate synthase activity is provided. In some embodiments, the polypeptide includes an amino acid sequence with at least 80% homology to SEQ ID NO: 2 and having the mutations H97A, S139G, N167G, P169A, R260A, N264Q, and G462D. In some embodiments of the the polypeptide includes an amino acid sequence with at least 80% homology to SEQ ID NO: 2 and having the mutations H97A, S139G, N167G, P169A, R260A, N264Q, and G462D, the polypeptide has at least 80% homology to residues 1-379 that make up the catalytic domain of SEQ ID NO: 2 (shown in FIG. 3). In other embodiments, the polypeptide includes an amino acid sequence with at least 90% homology to SEQ ID NO: 2 and having the mutations H97A, S139G, N167G, P169A, R260A, N264Q, and G462D. In some embodiments of the polypeptide includes an amino acid sequence with at least 90% homology to SEQ ID NO: 2 and having the mutations H97A, S139G, N167G, P169A, R260A, N264Q, and G462D, the polypeptide has at least 90% homology to residues 1-379 that make up the catalytic domain of SEQ ID NO: 2 (shown in FIG. 3). In some embodiments, the amino acid sequence of the genetically modified isopropylmalate synthase is obtained from *Enterobacter cloacae*. In certain embodiments, the polypeptide further includes the mutation M255L. In certain embodiments, the polypeptide is a purified polypeptide.

According to additional embodiments of the present disclosure, a genetically modified isopropylmalate synthase polypeptide having isopropylmalate synthase activity is provided. In some embodiments, the polypeptide includes an amino acid sequence with at least 80% homology to SEQ ID NO: 2 and having the mutations H97A, S139G, N167G, P169A, D348E, D350E, M353L, Q355N, and G462D. In some embodiments of the polypeptide includes an amino acid sequence with at least 80% homology to SEQ ID NO: 2 and having the mutations H97A, S139G, N167G, P169A, D348E, D350E, M353L, Q355N, and G462D, the polypeptide has at least 80% homology to residues 1-379 that make up the catalytic domain of SEQ ID NO: 2 (shown in FIG. 3). In other embodiments, the polypeptide includes an amino acid sequence with at least 90% homology to SEQ ID NO: 2 and having the mutations H97A, S139G, N167G, P169A, D348E, D350E, M353L, Q355N, and G462D. In some embodiments of the polypeptide includes an amino acid sequence with at least 90% homology to SEQ ID NO: 2 and having the mutations H97A, S139G, N167G, P169A, D348E, D350E, M353L, Q355N, and G462D, the polypeptide has at least 90% homology to residues 1-379 that make up the catalytic domain of SEQ ID NO: 2 (shown in FIG. 3). In some embodiments, the amino acid sequence of the genetically modified isopropylmalate synthase is obtained from *Enterobacter cloacae*. In certain embodiments, the polypeptide further includes the mutations M255L, R260A, and N264Q. In certain embodiments, the polypeptide is a purified polypeptide.

As used herein, two proteins (or a region of the proteins) are substantially homologous when the amino acid sequences have a certain percentage or more identity, e.g., at least about 50% 60%, 65%, 70%, 75%, 80%, 85%, 90%, 91%, 92%, 93%, 94%, 95%, 96%, 97%, 98%, or 99% identity. Percent homology can be determined as is known in the art. For example, to determine the percent identity of two amino acid sequences, the sequences are aligned for optimal comparison purposes (e.g., gaps can be introduced in one or both of a first and a second amino acid sequence for optimal alignment and non-homologous sequences can be disregarded for comparison purposes). The amino acid residues at corresponding amino acid positions are then compared. When a position in the first sequence is occupied by the same amino acid residue as the corresponding position in the second sequence, then the molecules are identical at that position (as used herein amino acid "identity" is equivalent to amino acid "homology"). As is known in the art, the percent identity between the two sequences is a function of the number of identical positions shared by the sequences, taking into account the number of gaps, and the length of each gap, which need to be introduced for optimal alignment of the two sequences. Sequence homology for polypeptides is typically measured using sequence analysis software.

When homologous is used in reference to proteins or peptides, it is recognized that residue positions that are not identical can often differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of homology may be adjusted upwards to correct for the conservative nature of the substitution. Means for making this adjustment are known to those of skill in the art. The following six groups each contain amino acids that are conservative substitutions for one another: 1) Serine (S), Threonine (T); 2) Aspartic Acid (D), Glutamic Acid (E); 3) Asparagine (N), Glutamine (Q); 4) Arginine (R), Lysine (K); 5) Isoleucine (I), Leucine (L), Methionine (M), Alanine (A), Valine (V), and 6) Phenylalanine (F), Tyrosine (Y), Tryptophan (W).

For example, amino acid sequences having the function of isopropylmalate synthase can be identified by performing a protein-protein BLAST (blastp) search of the non-redundant protein sequences (nr) database using the amino acid sequences of these proteins as query. The search can be conducted on the National Center for Biotechnology Information (NCBI) website (http//blast.ncbi.nlm.nih.gov) using default parameters. An alignment of amino acid sequences of isopropylmalate synthase from *E. coli* (LeuA), isopropylmalate synthase from *E. coli* with mutations H97A, S139G, N167G, P169A, and G462D (construct 614), isopropylmalate synthases from *Citrobacter freundii* with mutations H97A, S139G, N167G, P169A, and G462D (contruct 1409), isopropylmalate synthases from *Enterobacter cloacae* with mutations H97A, S139G, N167G, P169A, and G462D (construct 1414), isopropylmalate synthases from Leptospira biflexa (UniProtKB/Swiss-Prot Accession No. B0SN40), and isopropylmalate synthases from *Mycobacterium tuberculosis* (UniProtKB/Swiss-Prot Accession No. P9WQB3), showed 25-96% identical amno acids in their sequence, or alternately 42-97% homologous sequences (data not shown). As previously stated, the catalytic domain of isopropylmalate synthase from *Citrobacter freundii* and *Enterobacter cloacae* is made up of residues 1-379. Additionally, and without being bound by the theory, it is believed that the active site of isopropylmalate synthases from *Citrobacter freundii* and *Enterobacter cloacae* includes the following amino acid residues: R13, D14, Q17, L73, H97, F99, S139, E141, D142, N167, P169, D170, T171, H202, H204, E226, E234, R235, G237, N238, H300, D302, and Y311.

In embodiments, amino acid residues which are not believed to be essential for the functioning of isopropylmalate synthases from *Citrobacter freundii* and *Enterobacter cloacae* (e.g., residues that are outside of the catalytic domain (residues 1-379)) may be substituted either conservatively or non-conservatively, and such amino acid substitutions would likely not significantly diminish the functional properties of the modified isopropylmalate synthases as compared to isopropylmalate synthases from *Citrobacter freundii* with mutations H97A, S139G, N167G, P169A, and G462D (construct 1409) and isopropylmalate synthases from *Enterobacter cloacae* with mutations H97A, S139G, N167G, P169A, and G462D (construct 1414). In embodiments, most conservative and nonconservative amino acid substitutions for certain amino acid residues which are believed to form the active site of synthases from *Citrobacter freundii* and *Enterobacter cloacae* (e.g., residues R13, D14, Q17, L73, H97, S139, E141, N167, P169, T171, H202, H204, E226, E234, R235, G237, N238, H300, D302, and Y311), other than those specific amino acid substitutions described herein, will likely diminish the functional properties of the modified isopropylmalate synthases as compared to isopropylmalate synthases from *Citrobacter freundii* with mutations H97A, S139G, N167G, P169A, and G462D (construct 1409) and isopropylmalate synthases from *Enterobacter cloacae* with mutations H97A, S139G, N167G, P169A, and G462D (construct 1414). In embodiments, most conservative and nonconservative amino acid substitutions for certain amino acid residues which are believed to form the active site of synthases from *Citrobacter freundii* and *Enterobacter cloacae* (e.g., residues F99, D142, and D170), will likely not diminish the functional properties of the modified isopropylmalate synthases as compared to isopropylmalate synthases from *Citrobacter freundii* with mutations H97A, S139G, N167G, P169A, and G462D (construct 1409), isopropylmalate synthases from *Enterobacter cloacae* with mutations H97A, S139G, N167G, P169A, and G462D (construct 1414). In embodiments, most conservative and nonconservative amino acid substitutions for certain amino acid residues in the catalytic domain of isopropylmalate synthases from *Citrobacter freundii* and *Enterobacter cloacae* (e.g., residues L12-G15, Q17-L19, K28, L35, E44-P48, F55, L73, I81, A91, H97, S103, E117, V18, A129, S139, E141, A157, I159, N167, P169, T171, V172, P177, I198, S200, H202, H204, D206, G208, G221, A222, E226, G231, G233-R235, G237, N238, L241, I260, I266, P280, G289, S297, G298, H300-D302, Y311, P316, G320, S332, G333, and G345), other than those specific amino acid substitutions described herein, will likely diminish the functional properties of the modified isopropylmalate synthases as compared to isopropylmalate synthases from *Citrobacter freundii* with mutations H97A, S139G, N167G, P169A, and G462D (construct 1409) and isopropylmalate synthases from *Enterobacter cloacae* with mutations H97A, S139G, N167G, P169A, and G462D (construct 1414). In embodiments, most conservative and nonconservative amino acid substitutions for all other amino acid residues in the catalytic domain of isopropylmalate synthases from *Citrobacter freundii* and *Enterobacter cloacae* (e.g., all amino acid residues in the catalytic domain other than residues L12-G15, Q17-L19, K28, L35, E44-P48, F55, L73, I81, A91, H97, I103, E117, V18, A129, S139, E141, A157, I159, N167, P169, T171, V172, P177, I198, S200, H202, H204, D206, G208, G221, A222, E226, G231, G233-R235, G237, N238, L241, I260, I266, P280, G289, S297, G298, H300-D302, Y311, P316, G320, S332, G333, and G345), other than those specific amino acid substitutions described herein, will likely not diminish the functional properties of the modified isopropylmalate synthases as compared to isopropylmalate synthases from *Citrobacter freundii* with mutations H97A, S139G, N167G, P169A, and G462D (construct 1409) and isopropylmalate synthases from *Enterobacter cloacae* with mutations H97A, S139G, N167G, P169A, and G462D (construct 1414). It is believed that genetically modified isopropylmalate synthases from *Citrobacter freundii* and *Enterobacter cloacae* having the described substitutions would confer isopropylmalate synthase activity. Stated another way, it is believed that the amino acid substitutions described herein would not significantly diminish the functional properties of the modified isopropylmalate synthases from *Citrobacter freundii* and *Enterobacter cloacae* as compared to isopropylmalate synthases from *Citrobacter freundii* with mutations H97A, S139G, N167G, P169A, and G462D (construct 1409) and isopropylmalate synthases from *Enterobacter cloacae* with mutations H97A, S139G, N167G, P169A, and G462D (construct 1414), respectively.

The instantly-disclosed genetically modified isopropylmalate synthases with the improved properties, particularly with improved catalytic efficiency (i.e., $k_{cat}/K_m$) at capturing and condensing acetyl CoA and 2-ketooctanoate, were created through genetic modification in one of a variety of ways that are described herein. The terms "genetically modified," or "modified," as used herein, refer to the group of instantly disclosed genetically modified isopropylmalate synthases having an intentionally altered amino acid sequence, i.e., a "non-wild type" amino acid sequence, or to a microbial organism (depending upon placement of either term as an adjective) having a genome that has been intentionally altered as to (at least) the specific, modified isopropylmalate synthase(s) described herein, or both. Such alterations may be accomplished via recombinant technology, wherein one or more genes are transferred from a second, different microbial organism into a target microbial organism. Recombinant technology can be accomplished using fully synthetic DNA that is transferred to the target microbial organism using conventional methods. Such alterations may also be accomplished via engineered technology, wherein the nucleic acids within the target microbial organism are altered, generally via site-directed mutagenesis, resulting in the conversion of at least one nucleic acid to a different nucleic acid and therefore modification of one or more enzymes. Combinations of any of the above methods and those described throughout the application may also be employed. Thus, it will be understood that the instantly disclosed genetically modified isopropylmalate synthases can be used either in vivo, i.e., by a genetically modified microorganism, or in vitro.

In other embodiments, processes for preparing a $C_7$-$C_{11}$ 2-ketoacid are provided. In embodiments, the processes for preparing $C_7$-$C_{11}$ 2-ketoacids include providing at least one of a $C_4$-$C_{10}$ 2-ketoacid substrate with a series of enzymes that include a genetically-modified isopropylmalate synthase. In some embodiments, the processes include preparing a $C_7$-$C_{11}$ 2-ketoacid by providing a starting substrate and a series of enzymes that act on the substrate or product thereof. In embodiments, the series of enzymes include a genetically-modified isopropylmalate synthase of the instant disclosure. In some embodiments, the series of enzymes ultimately convert the substrate, using additional enzymes and steps, to the desired $C_7$-$C_{11}$ 2-ketoacid. The term "substrate" or "suitable substrate" refers to any substance or compound that is converted or meant to be converted into another compound by the action of an enzyme. The term includes not only a single compound, but also combinations of compounds, such as solutions, mixtures and other materials which contain at least one substrate, or derivatives thereof. Further, the term "substrate" encompasses not only compounds that provide a carbon source suitable for use as a starting material, such as any biomass derived sugar, but also intermediate and end product metabolites used in a pathway associated with a metabolically engineered microorganism as described herein.

The processes for preparing a $C_7$-$C_{11}$ 2-ketoacid may further include converting the $C_7$-$C_{11}$ 2-ketoacid, with even further additional enzymes and steps, to a desired $C_6$-$C_{10}$ aldehyde, $C_6$-$C_{10}$ alcohol, $C_6$-$C_{10}$ carboxylic acid, or $C_5$-$C_9$ alkane. These processes may be carried out biosynthetically in one of the described embodiments of a non-naturally occurring, i.e., genetically engineered, cell. For example, in illustrative, non-limiting embodiments, these processes may be carried out in a non-naturally occurring microbial organism. Alternatively, in other illustrative, non-limiting embodiments, production of the $C_7$-$C_{11}$ 2-ketoacid(s), $C_6$-$C_{10}$ aldehyde(s), $C_6$-$C_{10}$ alcohol(s), $C_6$-$C_{10}$ carboxylic acid(s), or $C_5$-$C_9$ alkane(s) may be carried out via in vitro methodology, typically beginning from a starting point that does not include a microbial organism.

Figure 2:
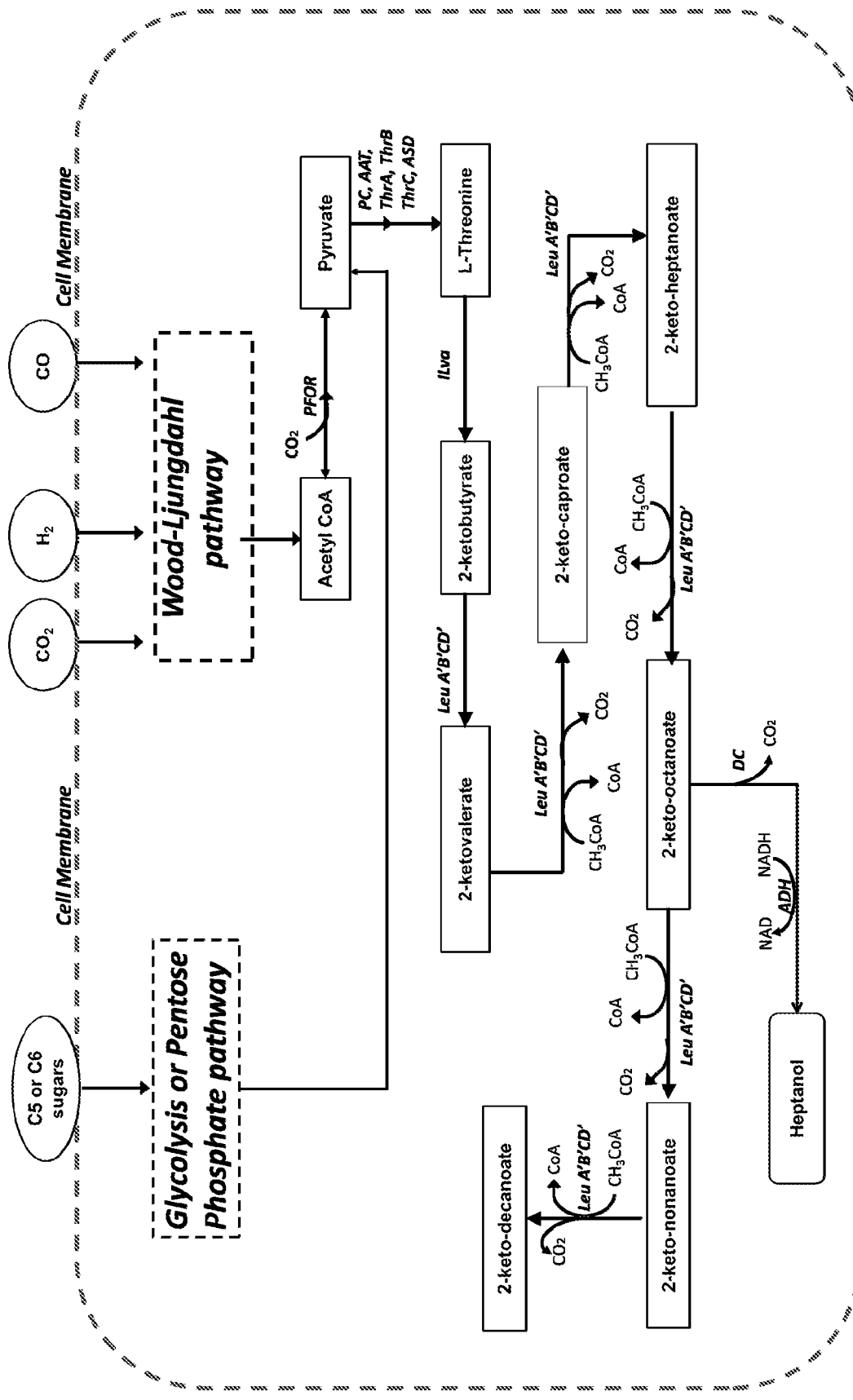
FIG. 2. Two pathways to produce 1-heptanol.

In some embodiments of the processes to prepare the $C_7$-$C_{11}$ 2-ketoacid(s), $C_6$-$C_{10}$ aldehyde(s), $C_6$-$C_{10}$ alcohol(s), $C_6$-$C_{10}$ carboxylic acid(s), or $C_5$-$C_9$ alkane(s), a selected carbon-containing substrate is converted first to pyruvate, and from pyruvate to either 2-ketobutyrate or, alternatively, to 2-ketoisovalerate, via the action of one or more enzymes and in one or more biochemical reactions (FIG. 2). More specifically, in embodiments, the carbon-containing substrate is provided and/or contacted with one or more enzymes in one or more biochemical reactions such that it is converted to either 2-ketobutyrate or 2-ketoisovalerate. The 2-ketobutyrate or 2-ketoisovalerate may then be converted, via chain elongation, to a $C_7$-$C_{11}$ 2-ketoacid, by the action of the enzymes, enzyme complexes, genetically modified enzymes, genetically modified enzyme complexes, or a combination thereof in the "+1" pathway (or the LeuABCD pathway, as it is termed with respect to the *E. coli* microbial organism), which is a portion of the non-natural leucine pathway (FIG. 1). In embodiments, the enzymes capable of accomplishing this chain elongation are identified herein as constituting: isopropylmalate synthase (e.g., a native isopropylmalate synthase such as *E. coli* isopropylmalate synthase, LeuA (GenBank Accession No. NC 000913.3 Gene ID: 947465), and/or a genetically modified isopropylmalate synthase having isopropylmalate synthase activity (e.g., the genetically modified isopropylmalate synthase having isopropylmalate synthase activity as previously described above, and/or as described by Marcheschi et. al. "A synthetic recursive "+1" pathway for carbon chain elongation." *ACS chemical biology* 2012, 7, 689-697, which is incorporated by reference in its entirety)); isopropylmalate dehydrogenase (e.g., a native isopropylmalate dehydrogenase, such as LeuB (GenBank: Accession No. NC 000913.3 Gene ID: 944798), and/or a genetically modified isopropylmalate dehydrogenase having isopropylmalate dehydrogenase activity, such as LeuB' (e.g., as described by Sanghani et al in WO2015089127A1, which is incorporated by reference in its entirety)); and/or isopropylmalate isomerase (e.g., a native LeuCD complex (i.e., two enzymes that, together, are termed isopropylmalate isomerase complex) (GenBank: Accession No. NC 000913.3 Gene ID: 945076 and Gene ID: 945642, respectively), and/or a genetically modified isopropylmalate isomerase having isopropylmalate isomerase activity (e.g., a genetically modified LeuCD' having isopropylmalate isomerase activity as described in U.S. Provisional Patent Application Ser. No. 62/402,569 filed Sep. 30, 2016, which is incorporated by reference in its entirety). In embodiments, the genetically modified isopropylmalate synthase having isopropylmalate synthase activity is as previously described above. The appropriate substrates, including intermediates and end product metabolites may be added at any point in the "+1" pathway (shown in FIG. 1) as would be known to one of ordinary skill in the art.

In embodiments, the genetically modified isopropylmalate synthase having isopropylmalate synthase activity can be as previously described above, and/or as described by Marcheschi et. al. "A synthetic recursive "+1" pathway for carbon chain elongation." *ACS chemical biology* 2012, 7, 689-697, which is incorporated by reference in its entirety. In certain embodiments, the genetically modified isopropylmalate synthase having isopropylmalate synthase activity can comprise a LeuA' variant having substitutions at one or more amino acid residue sights designated Phe-47 Leu-73, His-97, Phe-99, Ser-139, Asn-167, Pro-169, Asn-197, and/or Gly-462. One or more of these targeted amino acids is/are then substituted with the amino acids glycine, alanine, leucine, and/or valine, which can be performed by site-directed mutagenesis of the known isopropylmalate synthase of a selected organism, such as the LeuA gene of *E. coli* (GenBank: Accession No. NC_000913.3 Gene ID:947465). In certain aspects, embodiments the genetically modified LeuA' can include the following combination of substitutions: alanine for His-97, glycine for Ser-139, glycine for Asn-167, alanine for Pro-169, and/or aspartic acid for Gly-462. These genetically modified LeuA' variants are more efficient (higher $k_{cat}/K_m$) than the wild type enzyme in capturing 2-ketoacids of interest for catalysis, and thus can improve the overall efficiency of the relevant "+1" pathway.

In embodiments, the genetically modified isopropylmalate dehydrogenase having isopropylmalate dehydrogenase activity can be as described by Sanghani et al in WO2015089127A1, which is incorporated by reference in its entirety. In certain embodiments, the genetically modified isopropylmalate dehydrogenase having isopropylmalate dehydrogenase activity can comprise a LeuB' variant having substitutions at one or more amino acid residue sights designated Leu-96 and Val-198. One or more of these targeted amino acids is/are then substituted with the amino acids glycine, alanine, and/or valine, which can be performed by site-directed mutagenesis of the known isopropylmalate dehydrogenase of a selected organism, such as the LeuB gene of *E. coli* (GenBank: Accession No. NC_000913.3 Gene ID: 944798). In certain aspects, the genetically modified LeuB' can include the following substitutions: glycine for Leu-96; alanine for Val-198; alanine for Leu-96 and alanine for Val-198; glycine for Leu-96 and alanine for Val-198; glycine for Leu-96 and glycine for Val-198'; or alanine for Leu-96. These genetically modified LeuB' variants are more efficient (higher $k_{cat}/K_m$) than the wild type enzyme in converting 3-HM to the corresponding $C_7$-$C_{11}$ 2-ketoacid, and thus can improve the overall efficiency of the relevant "+1" pathway.

In embodiments, a genetically modified isopropyl isomerase having isopropyl isomerase activity can be as described in U.S. Provisional Patent Application Ser. No. 62/402,569 filed Sep. 30, 2016, which is incorporated by reference in its entirety. In certain embodiments, a genetically modified LeuCD' enzyme complexes include a number of altered amino acid sequences of a LeuCD enzyme complex. In embodiments, the altered amino acid sequences having been identified as exhibiting improved activity and catalytic efficiency (i.e., $k_{cat}/K_m$) at isomerizing longer chain 2-alkylmalates, such as e.g., $C_4$-$C_6$ 2-alkylmalates, to their corresponding 3-alkylmalates in comparison with the wild type *E. coli* LeuCD enzyme complex (LeuC: EcoGene Accession Number EG11576, Gene ID 945076; and LeuD: EcoGene Accession Number EB11575, Gene ID: 945642). Various sites within the wild type LeuC sequence and wild type LeuD sequence have been identified as key to obtaining the improvements. The sites within the wild type sequence of LeuC include Val-35, Leu-411, and combinations thereof. The sites within the wild type sequence of LeuD include Leu-31, His-88, and combinations thereof. In each alteration, changes are made wherein: alanine or glycine is substituted for Val-35 of LeuC; valine, alanine, or glycine is substituted for Leu-411 of LeuC; valine, alanine, or glycine is substituted for Leu-31 of LeuD; and/or serine or alanine is substituted for His-88 of LeuD. The substitutions can vary from single-site (i.e. single amino acid constituting three base pairs) substitution in either LeuC or LeuD, to a wide variety of multiple-site (e.g., from 2-4 sites) substitutions within both LeuC and LeuD. The substitutions can be performed by site-directed mutagenesis of the known wild type *E. coli* LeuCD enzyme complex.

In embodiments, a genetically modified LeuCD' enzyme complex include (a) a LeuC subunit and (b) a Leu D subunit. For example, in some embodiments, the LeuC subunit (a) is selected from the group consisting of: (1) a native LeuC subunit including an amino acid sequence; and (2) a genetically modified LeuC subunit including at least one modification wherein alanine, glycine, or valine is independently substituted for Val-35, Leu-411, or a combination thereof. In some embodiments of a genetically modified LeuCD' enzyme complexes, the LeuD subunit (b) is selected from the group consisting of: (1) a native LeuD subunit; and (2) a genetically modified LeuD subunit including at least one modification wherein alanine, glycine, valine, or serine is independently substituted for Leu-31, His-88, or a combination thereof. In some embodiments, a genetically modified LeuCD' enzyme complex includes a combination of (a)(1) and (b)(2), a combination of (a)(2) and (b)(2), or a combination of (a)(2) and (b)(1). Importantly, a genetically modified LeuCD' enzyme complex has isopropylmalate isomerase activity.

In certain embodiments of a genetically modified LeuCD' enzyme complex, at least one modification of the amino acid sequence of LeuC, (a)(2), is selected from the group consisting of: (i) alanine for Val-35; (ii) glycine for Val-35; (iii) alanine for Val-35 and valine for Leu-411; (iv) alanine for Val-35 and alanine for Leu-411; (v) alanine for Val-35 and glycine for Leu-411; and (vi) glycine for Val-35 and valine for Leu-411. In other embodiments of a genetically modified LeuCD enzyme complex, the at least one modification of the amino acid sequence of LeuD, (b)(2), is selected from the group consisting of: (i) alanine for Leu-31; (ii) glycine for Leu-31; (iii) valine for Leu-31; (iv) alanine for Leu-31 and serine for His-88; (v) glycine for Leu-31 and alanine for His-88; (vi) glycine for Leu-31 and serine for His-88; and (vii) valine for Leu-31 and alanine for His-88.

In some embodiments, a genetically modified LeuCD' enzyme complex comprises a combination of (a)(1) and (b)(2), and the at least one modification of the amino acid sequence of (b)(2) is glycine for Leu-31. In other embodiments, a genetically modified LeuCD' enzyme complex comprises a combination of (a)(2) and (b)(2), and the at least one modification of the amino acid sequence of (a)(2) is alanine for Val-35, and wherein the at least one modification of the amino acid sequence of (b)(2 is glycine for Leu-31. In some embodiments, a genetically modified LeuCD' enzyme complex comprises a combination of (a)(2) and (b)(2), the at least one modification of the amino acid sequence of (a)(2) is alanine for Val-35 and glycine for Leu-411, and the at least one modification of the amino acid sequence of (b)(2) is glycine for Leu-31.

Following chain elongation of the 2-ketobutyrate or 2-ketoisolvalerate, the $C_7$-$C_{11}$ 2-ketoacid may then be converted to a $C_6$-$C_{10}$ aldehyde by the action of at least one enzyme, such as, e.g., a thiamin dependent decarboxylase (e.g., a native and/or genetically modified thiamin dependent decarboxylase having decarboxylase activity). Specifically, the 2-ketyobutyrate or 2-ketoisovalerate may be provided and/or contacted with a native and/or genetically modified thiamin dependent decarboxylase having decarboxylase activity. In embodiments wherein a native or genetically modified thiamin dependent decarboxylase acts on the $C_7$-$C_{11}$ 2-ketoacid, the native or genetically modified thiamin dependent decarboxylase converts the $C_7$-$C_{11}$ 2-ketoacid to a $C_6$-$C_{10}$ aldehyde having one less carbon atom than the $C_7$-$C_{11}$ 2-ketoacid being converted. In embodiments, the thiamin dependent decarboxylase has thiamin dependent decarboxylase activity. Further disclosure regarding the modification and selection of thiamin dependent decarboxylase having thiamin dependent decarboxylase activity is included in co-pending International Publication Number WO 2015/089127, which is incorporated herein in its entirety by reference.

The $C_6$-$C_{10}$ aldehyde(s) may be used as is, in a variety of industrial applications, or may be employed as an intermediate and/or starting material for production of other chemicals. For example, the $C_6$-$C_{10}$ aldehyde(s) may be provided and/or contacted with an alcohol dehydrogenase (e.g., a native (Accession No. NC_001145.3, GeneID:855368) and/or genetically modified alcohol dehydrogenase) which converts the $C_6$-$C_{10}$ aldehyde to the corresponding $C_6$-$C_{10}$ alcohol. In embodiments, the alcohol dehydrogenase has alcohol dehydrogenase activity. Alternatively, the $C_6$-$C_{10}$ aldehyde(s) may be provided and/or contacted with an aldehyde deydrogenase (e.g., a native and/or genetically modified aldehyde dehydrogenase (Accession No. NM_000689.4)), which converts it to the corresponding $C_6$-$C_{10}$ carboxylic acid. In embodiments, the aldehyde dehydrogenase has aldehyde dehydrogenase activity. Finally, the $C_6$-$C_{10}$ aldehyde(s) may be contacted with a fatty aldehyde decarbonylase (e.g., a native and/or genetically modified fatty aldehyde decarbonylase (Accession No. NM_100101.3)), which converts it to the corresponding $C_{n-1}$ alkane. In embodiments, the fatty aldehyde decarbonylase has fatty aldehyde decarbonylase activity.

In preferred embodiments, the product, for example, a $C_6$-$C_{10}$ alcohol, a $C_6$-$C_{10}$ carboxylic acid, or a $C_5$-$C_9$ alkane is produced with desirably high specificity. This high specificity can be, e.g., preferably at least 25 percent (i.e., %), more preferably at least 40%, still more preferably at least 50%, and most preferably at least 70%, based on weight (i.e., wt) of total product (i.e., wt %), as the targeted product.

As noted hereinabove, the processes described herein may be carried out either in vivo or in vitro. An in vivo approach may be preferred for commercial scale production, although in some cases an in vitro approach may be suitable for commercial scale production. In embodiments, an in vitro approach may be particularly convenient for laboratory and general research purposes, such as, e.g., to carry out enzymatic assays. For example, desirable microbial organisms useful for large or commercial scale fermentative production of an enzyme-facilitated product, such as a $C_6$-$C_{10}$ alcohol or combination of $C_6$-$C_{10}$ alcohols, may be prepared. Such preparation may be carried out by inserting the DNA, or pieces of DNA, which encode the desired enzyme, from a first microbial organism into the genome of a second, microbial organism. In embodiments, the host microbial organism is known or believed to possess one or more desired metabolic pathways and/other desired features, using recombinant technology. In general, the in vivo approach employs a microbial organism's wild type metabolic pathway(s), first to convert a suitable carbon-containing substrate to pyruvate, and then to convert the pyruvate to 2-ketobutyrate or, alternatively, to 2-ketoisovalerate, in a varying number of biochemical reactions.

For example, the instantly disclosed genetically modified "+1" pathway enzyme complexes may be used and/or expressed as part of a metabolic pathway in a microbial organism that produces acetyl-CoA via either an anabolic (e.g., Wood-Ljungdahl) or catabolic (e.g., glycolysis, or a pentose phosphate pathway) route (FIG. 2). The $C_7$-$C_{11}$ 2-ketoacid may then be converted to the corresponding $C_6$-$C_{10}$ aldehyde having one less carbon by the action of at least one more enzyme, such as, e.g., a thiamin dependent decarboxylase (e.g., a native and/or genetically modified thiamin dependent decarboxylase having decarboxylase activity). In some embodiments, the $C_6$-$C_{10}$ aldehyde may be further reacted with appropriate enzymes to form a $C_6$-$C_{10}$ alcohol, $C_6$-$C_{10}$ carboxylic acid, or $C_5$-$C_9$ alkane. Because of the specific alterations in its amino acid sequence that are described herein, the genetically modified isopropylmalate synthases that are described herein offer some significant differences in specificity and catalytic efficiency to various substrates, and this alteration in specificity offers important advantages in terms of product yields and the reduction or elimination of undesirable and/or competing side products. For example and as previously mentioned, due to the additional mutations in the catalytic site, the genetically modified isopropylmalate synthases exhibit improved activity and catalytic efficiency (i.e., $k_{cat}/K_m$) at capturing and condensing acetyl CoA and longer chain 2-ketoacids, particularly 2-ketooctanoate, as compared to a previously disclosed genetically modified isopropylmalate synthase from *E. coli* having mutations H97A, S139G, N167G, P169A, and G462D.

In some embodiments, the selected microbial organism may possess a Wood-Ljungdahl pathway, also known as a "synthesis gas (syngas) fixation pathway," wherein syngas is converted to acetyl CoA, as shown in FIG. 2. Such may be carried out by certain acetate-producing bacteria species, such as those of the genus *Clostridium*, including but not limited to, in particular, *Clostridium ljungdahlii* (i.e., *C. ljungdahlii*). In the Wood-Ljungdahl pathway, conversion of the syngas to acetyl CoA generally includes reduction of carbon dioxide to carbon monoxide, and then to acetyl CoA via the action of two enzymes, carbon monoxide dehydrogenase and actetyl CoA synthase. Carbon monoxide dehydrogenase, which catalyzes the reduction of the carbon dioxide, and acetyl CoA synthase, which combines the resulting carbon monoxide with a methyl group to form acetyl CoA. From this point the acetyl CoA continues on another pathway wherein it is converted to pyruvate via reduction by PFO (i.e., ferredoxin oxidoreductase). Such pathways may be present in microbial organisms including, for example, *Clostridium, Escherichia coli* (i.e., *E. coli*), *Azospirillum, Bacillus, Saccharomyces*, and *Corynebacterium*. In alternative embodiments, a suitable (non-syngas) carbon-containing substrate, such as a C5 or C6 sugar (glucose, sucrose, pentose, or a combination thereof), may be converted directly to pyruvate via one of the sugar catabolism pathways, such as a glycolysis or pentose phosphate pathway.

Upon conversion of the syngas or non-syngas substrate to pyruvate, the pyruvate may be converted first to L-threonine, via PC (i.e., pyruvate carboxylase); AAT (i.e., aspartate aminotransferase); ThrABC (which includes: ThrA, which is a bifunctional aspartokinase/homoserine dehydrogenase; ThrB, which is homoserine kinase; and ThrC, which is threonine synthase); and ASD (i.e., aspartate semialdehyde dehydrogenase). The L-threonine may then be converted to 2-ketobutyrate via ILva (i.e., threonine dehydratase). In an alternative embodiment, the pyruvate may be converted to 2-ketoisovalerate via the activities of llvBN/llvGM, llvC, and llvD.

Following production of 2-ketobutyrate or 2-ketoisovalerate, genetic modification of the native "+1" pathway portion of the non-natural leucine biosynthesis pathway operates to effect conversion to a $C_7$-$C_{11}$ 2-ketoacid via one or more biochemical reactions. In an in vivo approach, several biochemical reactions are involved and employ at least one native or modified (i.e., endogenous or exogenous) enzyme, enzyme complex, or combination thereof of the "+1 pathway" to convert 2-ketobutyrate or 2-ketoisovalerate to a desired $C_7$-$C_{11}$ 2-ketoacid (FIG. 1). For example, in embodiments, 2-ketobutyrate is converted first to 2-ketovalerate, then to 2-ketocaproate, then to 2-ketoheptanoate or up to 2-keto-undecanoate, i.e., a desired $C_7$-$C_{11}$ 2-ketoacid depending upon the desired final product, as chain-lengthening occurs. Alternatively, 2-ketoisovalerate is converted first to 2-ketoisocaproate, then to 2-ketoisoheptanoate, and so forth. The native enzymes or genetically modified enzymes accomplishing this chain elongation may include an isopropylmalate synthase (e.g., a native isopropylmalate synthase and/or a genetically modified isopropylmalate synthase having isopropylmalate synthase activity), an isopropylmalate deydrogenase (e.g., a native isopropylmalate dehydrogenase and/or a genetically modified isopropylmalate dehydrogenase having isopropylmalate dehydrogenase activity), and/or an isopropylmalate isomerase (e.g., a native isopropylmalate isomerase and/or a genetically modified isopropylmalate isomerase having isopropylmalate isomerase activity). In some embodiments, only one enzyme, enzyme complex or combination thereof is genetically modified. For example, in specific embodiments, only isopropylmalate synthase is genetically modified to obtain acceptable or desirable production of a $C_7$-$C_{11}$ 2-ketoacid beginning with 2-ketobutyrate or 2-ketoisovalerate. Further disclosure regarding modification of this portion of the non-natural leucine biosynthesis pathway is included in co-pending International WO2015089127, which is incorporated herein in its entirety by reference, and is also discussed previously above. In certain embodiments, a genetically modified LeuA (i.e., LeuA'), a genetically modified LeuB (i.e., LeuB'), a genetically modified LeuCD (i.e., LeuCD'), or combinations thereof can be utilized, as described in the referenced patent application.

Once an elongated $C_7$-$C_{11}$ 2-ketoacid is formed, such may be used as is, or converted to a $C_6$-$C_{10}$ aldehyde. For such conversion, a thiamin dependent decarboxylase (e.g., a native and/or genetically modified thiamin dependent decarboxylase) is employed, resulting in a $C_6$-$C_{10}$ aldehyde having one less carbon atom than the $C_7$-$C_{11}$ 2-ketoacid being converted. $C_6$-$C_{10}$ aldehydes enjoy wide applicability, such as, e.g., as starting substrates or intermediates in producing $C_6$-$C_{10}$ alcohols, $C_6$-$C_{10}$ carboxylic acids, $C_5$-$C_9$ alkanes, and combinations thereof, as described hereinabove. Production of a $C_6$-$C_{10}$ alcohol is illustrated in FIG. 1.

In order to enable a non-native organism to carry out some portion of the conversions in vivo as defined hereinabove, for example, to produce the $C_7$-$C_{11}$ 2-ketoacid(s), $C_6$-$C_{10}$ aldehyde(s), $C_6$-$C_{10}$ alcohol(s), $C_6$-$C_{10}$ carboxylic acid(s), or $C_5$-$C_9$ alkane(s), it is desirable to perform protocols similar to that described herein. In general, the working examples show genetic modification involving engineering to alter one or more nucleic acid base(s) in a given codon in order to alter the enzyme of which the nucleic acid base(s) is/are a part. Such may be used simply to produce the modified enzyme for, e.g., in vitro assay purposes. In contrast, the genome of a host microbial organism may be preferably altered for a larger scale production strain.

The following methodology, designed for in vitro enzyme production, may be carried out as is generally understood by those skilled in the art. In general, a suitable database, such as GenBank, is used to obtain the genetic codes for the wild type enzyme(s), followed by identification of the codons suitable for modification. This identification may be used as the basis for art-known methods of protein engineering, wherein computer molecular modeling identifies and also enables differentiation of structural locations at which modifications of enzyme/substrate interfaces may be effectively employed. A given desirable modification is then performed, using a molecular biology technique wherein the alteration(s) of the nucleic acid base(s) is/are done via site-directed mutagenesis. The variant-type enzymes must then be subjected to purification to separate out non-targeted proteins, leaving a purified enzyme that will exhibit a higher-than-wild type catalytic efficiency. This can be appropriately assayed in vitro, according to the methodology most suitable for the given particular enzyme. An assayed enzyme that is shown to have a desirable level of catalytic efficiency is thereby confirmed to be the product of a desirable genetic modification, and may be used for in vitro production methods, such as e.g., for the in vitro production and/or conversion of a given $C_7$-$C_{11}$ 2-ketoacid (such as e.g., 2-ketononoate), $C_6$-$C_{10}$ aldehyde (such as e.g., octanal), and/or a product made from the $C_6$-$C_{10}$ aldehyde (such as e.g., a $C_6$-$C_{10}$ alcohol, carboxylic acid, or a $C_5$-$C_9$ alkane).

Therefore, in some embodiments a process for preparing a $C_7$-$C_{11}$ 2-ketoacid includes: (I) providing at least one of a $C_4$-$C_{10}$ 2-ketoacid substrate with (A) a genetically modified isopropylmalate synthase having isopropylmalate synthase activity, (B) an isopropylmalate dehydrogenase having isopropylmalate dehydrogenase activity (e.g., a native and/or genetically modified isopropylmalate dehydrogenase having isopropylmalate dehydrogenase activity), and (C) an isopropyl isomerase having isopropyl isomerase activity (e.g., a native and/or genetically modified isopropyl isomerase having isopropyl isomerase activity), under conditions that the at least one of the $C_4$-$C_{10}$ 2-ketoacid substrate is converted to the $C_7$-$C_{11}$ 2-ketoacid. In some embodiments, the process can further include a native isopropylmalate synthase. In some embodiments, the conversion of the least one $C_4$-$C_{10}$ 2-ketoacid substrate to the $C_7$-$C_{11}$ 2-ketoacid occurs via one or more biochemical reactions. The biochemical reactions may independently occur within or outside of a genetically modified microbial organism. In certain embodiments, the $C_4$-$C_{10}$ 2-ketoacid substrate includes 2-ketobutyrate, while in other embodiments the $C_4$-$C_{10}$ 2-ketoacid substrate includes 2-ketoisovalerate. In even further embodiments, the C4-C10 2-ketoacid substrate includes 2-methyl-2-ketopentanoate.

In some embodiments of a process for preparing a $C_7$-$C_{11}$ 2-ketoacid, the genetically modified isopropylmalate synthase having isopropylmalate synthase includes an amino acid sequence with at least 80% homology to SEQ ID NO: 1 and having the mutations H97A, S139G, N167G, P169A, G181A, A182G, G210A, A214S, and G462D. In some embodiments of a genetically modified isopropylmalate synthase having isopropylmalate synthase that includes an amino acid sequence with at least 80% homology to SEQ ID NO: 1 and having the mutations H97A, S139G, N167G, P169A, G181A, A182G, G210A, A214S, and G462D, the isopropylmalate synthase has at least 80% homology to residues 1-379 that make up the catalytic domain of SEQ ID NO: 1 (shown in FIG. 3). In other embodiments, the genetically modified isopropylmalate synthase having isopropylmalate synthase activity includes an amino acid sequence with at least 90% homology to SEQ ID NO: 1 and having the mutations H97A, S139G, N167G, P169A, G181A, A182G, G210A, A214S, and G462D. In some embodiments of a genetically modified isopropylmalate synthase having isopropylmalate activity that includes an amino acid sequence with at least 90% homology to SEQ ID NO: 1 and having the mutations H97A, S139G, N167G, P169A, G181A, A182G, G210A, A214S, and G462D, the isopropylmalate synthase has at least 90% homology to residues 1-379 that make up the catalytic domain of SEQ ID NO: 1 (shown in FIG. 3). In some embodiments, the amino acid sequence of the genetically modified isopropylmalate synthase is obtained from *Citrobacter freundii*. In certain embodiments, the genetically modified isopropylmalate synthase further include the mutations Q258H and R260A.

According to other embodiments of a process for preparing a $C_7$-$C_{11}$ 2-ketoacid, the genetically modified isopropylmalate synthase having isopropylmalate synthase activity includes an amino acid sequence with at least 80% homology to SEQ ID NO: 2 and having the mutations H97A, S139G, N167G, P169A, R260A, N264Q, and G462D. In some embodiments of the genetically modified isopropylmalate synthase having isopropylmalate synthase activity that includes an amino acid sequence with at least 80% homology to SEQ ID NO: 2 and having the mutations H97A, S139G, N167G, P169A, R260A, N264Q, and G462D, the isopropylmalate synthase has at least 80% homology to residues 1-379 that make up the catalytic domain of SEQ ID NO: 2 (shown in FIG. 3). In other embodiments, the isopropylmalate synthase includes an amino acid sequence with at least 90% homology to SEQ ID NO: 2 and having the mutations H97A, S139G, N167G, P169A, R260A, N264Q, and G462D. In some embodiments of the genetically modified isopropylmalate synthase having isopropylmalate synthase activity that includes an amino acid sequence with at least 90% homology to SEQ ID NO: 2 and having the mutations H97A, S139G, N167G, P169A, R260A, N264Q, and G462D, the isopropylmalate synthase has at least 90% homology to residues 1-379 that make up the catalytic domain of SEQ ID NO: 2 (shown in FIG. 3). In some embodiments, the amino acid sequence of the genetically modified isopropylmalate synthase is obtained from *Enterobacter cloacae*. In certain embodiments, the isopropylmalate synthase further includes the mutation M255L.

According to further embodiments of a process for preparing a C7-C11 2-ketoacid, the genetically modified isopropylmalate synthase having isopropylmalate synthase activity includes an amino acid sequence with at least 80% homology to SEQ ID NO: 2 and having the mutations H97A, S139G, N167G, P169A, D348E, D350E, M353L, Q355N, and G462D. In some embodiments of the genetically modified isopropylmalate synthase having isopropylmalate synthase activity that includes an amino acid sequence with at least 80% homology to SEQ ID NO: 2 and having the mutations H97A, S139G, N167G, P169A, D348E, D350E, M353L, Q355N, and G462D, the isopropylmalate synthase has at least 80% homology to residues 1-379 that make up the catalytic domain of SEQ ID NO: 2 (shown in FIG. 3). In other embodiments, the isopropylmalate synthase includes an amino acid sequence with at least 90% homology to SEQ ID NO: 2 and having the mutations H97A, S139G, N167G, P169A, D348E, D350E, M353L, Q355N, and G462D. In some embodiments of the isopropylmalate synthase that includes an amino acid sequence with at least 90% homology to SEQ ID NO: 2 and having the mutations H97A, S139G, N167G, P169A, D348E, D350E, M353L, Q355N, and G462D, the isopropylmalate synthase has at least 90% homology to residues 1-379 that make up the catalytic domain of SEQ ID NO: 2 (shown in FIG. 3) In some embodiments, the amino acid sequence of the genetically modified isopropylmalate synthase is obtained from *Enterobacter cloacae*. In certain embodiments, the isopropylmalate synthase further includes the mutations M255L, R260A, and N264Q.

In some embodiments of a process for preparing a $C_7$-$C_{11}$ 2-ketoacid, the process further include: (II) providing the $C_7$-$C_{11}$ 2-ketoacid with a thiamin dependent decarboxylase (e.g., a native and/or genetically modified thiamin dependent decarboxylase having thiamin dependent decarboxylase activity), under conditions that the $C_7$-$C_{11}$ 2-ketoacid is converted to a $C_6$-$C_{10}$ aldehyde having one less carbon atom than the $C_7$-$C_{11}$ 2-ketoacid being converted.

In further embodiments of a process for preparing a $C_7$-$C_{11}$ 2-ketoacid, the process even further includes: (III) providing the $C_6$-$C_{10}$ aldehyde with an alcohol dehydronase (e.g., a native and/or genetically modified alcohol dehydronase having alcohol dehydrogenase activity), under conditions that the $C_6$-$C_{10}$ aldehyde is converted to a corresponding $C_6$-$C_{10}$ alcohol. In other embodiments, the process includes: (III) providing the $C_6$-$C_{10}$ aldehyde with an aldehyde dehydrogenase (e.g., a native and/or genetically modified aldehyde dehydrogenase having aldehyde dehydrogenase activity), under conditions that the $C_6$-$C_{10}$ aldehyde is converted to a corresponding $C_6$-$C_{10}$ carboxylic acid. In certain embodiments, the process includes: (III) providing the $C_6$-$C_{10}$ aldehyde with a fatty aldehyde decarbonylase (e.g., a native and/or genetically modified fatty aldehyde decarbonylase having fatty aldehyde decarbonylase activity), under conditions that the $C_6$-$C_{10}$ aldehyde is converted to a corresponding $C_{n-1}$ alkane.

In order to enable a non-native organism to carry out some portion of the conversions in vivo as defined hereinabove, for example, to produce the $C_6$-$C_{10}$ aldehydes and/or $C_6$-$C_{10}$ alcohols, it is desirable to perform protocols similar to that described hereunder. In general the Examples included herewith involve isopropylmalate synthase enzyme engineering to alter the amino acids in order to modify enzyme functionality, particularly in terms of activity and/or specificity. This alteration in the amino acids may be used to produce modified enzyme for small scale purposes, for example, for in vitro assays, or may be the basis for genome modification in order to produce a strain of microbial organisms suitable for larger scale production.

The methodology may be carried out as is understood by those skilled in the art. In general, a suitable database, such as GenBank, is used to obtain the genetic codes for the native enzyme(s), followed by identification of the codons suitable for modification. This identification may be used as the basis for art-known methods of protein engineering, wherein computer molecular modeling identifies and also enables differentiation of structural locations at which modifications of enzyme/substrate interfaces may be effectively employed. A given desirable modification is then performed, using a molecular biology technique called site-directed mutagenesis. The modified gene is then cloned into a replicative plasmid vector which, when transformed into a host microbial organism such as *E. coli* or *Clostridium* species, enables the production of enzymes having a higher-than-native catalytic efficiency. The *E. coli* or *Clostridium* cells containing the targeted variant enzyme also produce other native proteins. Therefore, the variant-type enzymes must then be subjected to purification to separate out non-targeted proteins and general cell structures, leaving a purified enzyme that will exhibit a higher-than-native, i.e., higher than wild type, catalytic efficiency. Catalytic efficiency can be appropriately assayed in vitro, according methodologies suited to the particular enzyme. An assayed enzyme that is shown to have a desirable level of catalytic efficiency is thereby confirmed to be the product of a desirable genetic modification, and may be used for in vitro production methods. For example, such an enzyme may be used for the in vitro production of a given $C_7$-$C_{11}$ 2-ketoacid, and/or a $C_6$-$C_{10}$ aldehyde, and/or a product made from the $C_6$-$C_{10}$ aldehyde, such as a $C_6$-$C_{10}$ alcohol, carboxylic acid, or a corresponding $C_{5-9}$ alkane.

A particular application for the above-described methodology is to produce a desirable microbial organism for large or otherwise commercial scale fermentative production of an enzyme-facilitated product, such as a $C_6$-$C_{10}$ aldehyde or one of the $C_6$-$C_{10}$ products that may be prepared therefrom. Such preparation may be carried out by inserting the DNA, or pieces of DNA, which encode for the desired improved enzyme into the genome of a second microbial organism known or believed to possess other desirable characteristics, such as, for example, capability to produce pyruvate (or acetyl CoA) from a particular carbon-containing substrate, or other advantageous trait(s). Thus, the second microbial organism is now genetically-modified, in that it produces a genetically modified enzyme.

In another embodiment, it is also possible to simply identify a microbial organism having native enzymes that are useful in a desired pathway, and either use that microbial organism itself as a starting microbial organism, or transfer the appropriate enzyme-encoding portion of the genome(s) of such microbial organism(s) into the genome of the organism that has been already identified as being useful for large scale fermentation production. An example of this would be to select a microbial organism that produces a suitable native thiamin dependent decarboxylase (i.e., DC) and native alcohol dehydrogenase (i.e., ADH). That microbial organism can then be used either as a starting organism or as a transformant organism to prepare a genetically modified microbial organism to produce a $C_6$-$C_{10}$ alcohol at higher yields or specificity than wild type microbial organisms.

Therefore, in some embodiments, a microbial organism including a genetically modified isopropylmalate synthase having isopropylmalate synthase activity is provided. In some embodiments of a microbial organism including a genetically modified isopropylmalate synthase, the isopropylmalate synthase includes an amino acid sequence with at least 80% homology to SEQ ID NO: 1 and having the mutations H97A, S139G, N167G, P169A, G181A, A182G, G210A, A214S, and G462D. In some embodiments of an isopropylmalate synthase that includes an amino acid sequence with at least 80% homology to SEQ ID NO: 1 and having the mutations H97A, S139G, N167G, P169A, G181A, A182G, G210A, A214S, and G462D, the isopropylmalate synthase has at least 80% homology to residues 1-379 that make up the catalytic domain of SEQ ID NO: 1

(shown in FIG. 3) In other embodiments, isopropylmalate synthase includes an amino acid sequence with at least 90% homology to SEQ ID NO: 1 and having the mutations H97A, S139G, N167G, P169A, G181A, A182G, G210A, A214S, and G462D. In some embodiments of an isopropylmalate synthase that includes an amino acid sequence with at least 90% homology to SEQ ID NO: 1 and having the mutations H97A, S139G, N167G, P169A, G181A, A182G, G210A, A214S, and G462D, the isopropylmalate synthase has at least 90% homology to residues 1-379 that make up the catalytic domain of SEQ ID NO: 1 (shown in FIG. 3). In some embodiments, the amino acid sequence of the genetically modified isopropylmalate synthase is obtained from *Citrobacter freundii*. In certain embodiments, the genetically modified isopropylmalate synthase further includes the mutations Q258H and R260A. The genetically modified isopropylmalate synthase is expressed in the microorganism and has isopropylmalate isomerase activity. In certain embodiments, the microorganism is *Citrobacter freundii*. In other embodiments, the microorganism is *Escherichia coli* or a *Clostridium* species.

In some embodiments of a microbial organism including a genetically modified isopropylmalate synthase, the isopropylmalate synthase includes an amino acid sequence with at least 80% homology to SEQ ID NO: 2 and having the mutations H97A, S139G, N167G, P169A, R260A, N264Q, and G462D. In some embodiments of an isopropylmalate synthase that includes an amino acid sequence with at least 80% homology to SEQ ID NO: 2 and having the mutations H97A, S139G, N167G, P169A, R260A, N264Q, and G462D, the isopropylmalate synthase has at least 80% homology to residues 1-379 that make up the catalytic domain of SEQ ID NO: 2 (shown in FIG. 3). In other embodiments, the isopropylmalate synthase includes an amino acid sequence with at least 90% homology to SEQ ID NO: 2 and having the mutations H97A, S139G, N167G, P169A, R260A, N264Q, and G462D. In some embodiments of an isopropylmalate synthase includes an amino acid sequence with at least 90% homology to SEQ ID NO: 2 and having the mutations H97A, S139G, N167G, P169A, R260A, N264Q, and G462D, the isopropylmalate synthase has at least 90% homology to residues 1-379 that make up the catalytic domain of SEQ ID NO: 2 (shown in FIG. 3). In some embodiments, the amino acid sequence of the genetically modified isopropylmalate synthase is obtained from *Enterobacter cloacae*. In certain embodiments, the isopropylmalate synthase further includes the mutation M255L. The genetically modified isopropylmalate synthase is expressed in the microorganism and has isopropylmalate isomerase activity. In certain embodiments, the microorganism is *Enterobacter cloacae*. In other embodiments, the microorganism is *Escherichia coli* or a *Clostridium* species.

In other embodiments of a microbial organism including a genetically modified isopropylmalate synthase, the isopropylmalate synthase includes an amino acid sequence with at least 80% homology to SEQ ID NO: 2 and having the mutations H97A, S139G, N167G, P169A, D348E, D350E, M353L, Q355N, and G462D. In some embodiments of an isopropylmalate synthase that includes an amino acid sequence with at least 80% homology to SEQ ID NO: 2 and having the mutations H97A, S139G, N167G, P169A, D348E, D350E, M353L, Q355N, and G462D, the isopropylmalate synthase has at least 80% homology to residues 1-379 that make up the catalytic domain of SEQ ID NO: 2 (shown in FIG. 3). In other embodiments, the isopropylmalate synthase includes an amino acid sequence with at least 90% homology to SEQ ID NO: 2 and having the mutations H97A, S139G, N167G, P169A, D348E, D350E, M353L, Q355N, and G462D. In some embodiment of an isopropylmalate synthase includes an amino acid sequence with at least 90% homology to SEQ ID NO: 2 and having the mutations H97A, S139G, N167G, P169A, D348E, D350E, M353L, Q355N, and G462D, the isopropylmalate synthase has at least 90% homology to residues 1-379 that make up the catalytic domain of SEQ ID NO: 2 (shown in FIG. 3). In some embodiments, the amino acid sequence of the genetically modified isopropylmalate synthase is obtained from *Enterobacter cloacae*. In certain embodiments, the isopropylmalate synthase further includes the mutations M255L, R260A, and N264Q. The genetically modified isopropylmalate synthase is expressed in the microorganism and has isopropylmalate isomerase activity. In certain embodiments, the microorganism is *Enterobacter cloacae*. In other embodiments, the microorganism is *Escherichia coli* or a *Clostridium* species.

EXAMPLES

Preparing the Genetically Modified isopropylmalate Synthases Having Increased Catalytic Activity Against 2-ketohexanoate and 2-ketooctanoate.

During 2-ketononanoate biosynthesis by the recursive activity of the "+1" pathway of the leucine biosynthetic pathway, isopropylmalate synthase captures and condenses acetyl CoA and 2-ketoacids of varying length. For efficient biosynthesis of 2-ketononanoate, it is desired that isopropylmalate synthase(s) efficiently captures 2-ketobutyrate, 2-ketovalerate, 2-ketohexanoate, 2-ketoheptanoate, and/or 2-ketooctanoate, with acetyl CoA, thereby generating the corresponding 2-alkylmalate products (intermediate II in FIG. 1). The native isopropylmalate synthase of *E. coli* and other microbial organisms are relatively inefficient in capturing longer nonnatural 2-ketoacid substrates. To improve the activity of native isopropylmalate synthase in capturing longer 2-ketoacids for catalysis, the active site of isopropylmalate synthase was modified using protein engineering techniques as described hereinbelow.

A Blast search was performed on the NCBI site to identify isopropylmalate synthases that were homologous to the *E. coli* isopropylmalate synthase (Gene accession no. EG11226). From more than 1000 sequences that varied in homology from 23-96% with the *E. coli* enzyme, isopropylmalate synthases from five microbial organisms were selected for protein engineering and their gene sequences downloaded from GenBank (Table 1). The open reading frame of each of the downloaded isopropylmalate synthase was translated in silico and the active site residues identified by alignment with the *Mycobacterium tuberculosis* isopropylmalate synthase, the structure of which has been reported earlier (Koon, N.; Squire, C. J.; Baker, E. N. Crystal structure of LeuA from *Mycobacterium tuberculosis*, a key enzyme in leucine biosynthesis. *Proceedings of the National Academy of Sciences of the United States of America* 2004, 101, 8295-8300.). Active site residues His-97, Ser-139, Asn-167, Pro-169, and Gly-462 that were modified earlier in *E. coli* isopropylmalate synthase (Marcheschi, R. J.; Li, H.; Zhang, K.; Noey, E. L.; Kim, S.; Chaubey, A.; Houk, K. N.; Liao, J. C. A synthetic recursive "+1" pathway for carbon chain elongation. *ACS chemical biology* 2012, 7, 689-697) were identified in the sequence of five selected isopropylmalate synthases from five different species of microbial organisms and modified as shown in Table 1.

TABLE 1

Activity of Isopropylmalate synthase (IPMS) variants from 1st round of engineering

| Construct | | Specific activity (nmol · min$^{-1}$ · ug$^{-1}$) | | |
|---|---|---|---|---|
| No. | Substitutions | 2-KBut | 2-KHex | 2-KOct |
| *E. coli* (Gene Accession No. EG11226) | | | | |
| 1 | Native | 5.5 ± 0.1 | 0.06 ± 0.00 | 0.02 ± 0.00 |
| 614 | H97A/S139G/N167G/P169A/G462D | 2.4 ± 0.0 | 4.2 ± 0.08 | 2.5 ± 0.01 |
| *Clostridium ljungdahlii* (Gene Accession No. WP_013237570.1) | | | | |
| 70 | Native | 0.6 ± 0.01 | 0.01 ± 0.00 | 0.01 ± 0.00 |
| 71 | H109A | 0.04 ± 0.00 | 0.01 ± 0.00 | 0.01 ± 0.00 |
| 73 | N179G | 0.1 ± 0.0 | 0.02 ± 0.0 | 0.01 ± 0.0 |
| 74 | P181A | 0.3 ± 0.00 | 0.01 ± 0.00 | 0.01 ± 0.0 |
| 77 | H109A/S151G/N179G/P181A | No activity | No activity | No activity |
| *Citrobacter freundii* MGH 56 (Gene Accession No. KDF09799) | | | | |
| 1403 | G462D | 3.6 ± 0.02 | 0.00 | 0.00 |
| 1404 | S139G/G462D | 2.3 ± 003 | 0.1 ± 0.01 | 0.00 |
| 1405 | L73A/S139G/G462D | 0.7 ± 0.00 | 0.1 ± 0.02 | 0.1 ± 0.03 |
| 1406 | H97A/S139G/N167G/G462D | 0.01 ± 0.00 | 0.00 ± 0.00 | 0.00 |
| 1407 | H97A/S139G/G462D | 0.5 ± 0.00 | 0.10 ± 0.00 | 0.08 ± 0.00 |
| 1408 | L73G/H97A/S139G/G462D | 0.1 ± 0.01 | 0.00 | 0.00 |
| 1409 | H97A/S139G/N167G/P169A/G462D | 0.3 ± 0.00 | 0.8 ± 0.01 | 0.4 ± 0.0 |
| *Enterobacter cloacae* (Gene Accession No. WP_014830637) | | | | |
| 1410 | S139G/G462D | 1.1 ± 0.00 | 0.05 ± 0.00 | 0.00 |
| 1411 | L73A/S139G/G462D | 0.4 ± 0.003 | 0.04 ± 0.006 | 0.00 |
| 1412 | H97A/S139G/G462D | 1.4 ± 0.002 | 0.4 ± 0.2 | 0.3 ± 0.00 |
| 1413 | H97A/S139G/N167G/G462D | 0.2 ± 0.00 | 0.03 ± 0.00 | 0.06 ± 0.01 |
| 1414 | H97A/S139G/N167G/P169A/G462D | 0.9 ± 0.00 | 4.0 ± 0.02 | 1.8 ± 0.01 |
| *Raoultella ornithinolytica* (Gene Accession No KAJ94701) | | | | |
| 1415 | G462D | >2.3 | 0.02 ± 0.00 | 0.00 |
| 1416 | L73A/G462D | 1.3 ± 0.01 | 0.02 ± 0.00 | 0.00 |
| 1417 | L73G/G462D | 1.7 ± 0.01 | 0.1 ± 0.00 | 0.00 |
| 1418 | H97A/G462D | 0.2 ± 0.07 | 0.00 | 0.00 |
| 1419 | S139G/G462D | 2.0 ± 0.02 | 0.1 ± 0.00 | 0.1 ± 0.00 |
| 1420 | H97A/S139G/G462D | 1.5 ± 0.00 | 0.01 ± 0.00 | 0.00 |
| 1421 | L73G/S139G/G462D | 0.3 ± 0.01 | 0.00 | 0.00 |
| 1422 | L73A/S139G/G462D | 0.9 ± 0.07 | 0.3 ± 0.05 | 0.00 |
| 1423 | L73G/H97A/S139G/G462D | 0.3 ± 0.00 | 0.00 | 0.00 |
| 1425 | H97A/S139G/N167G/P169A/G462D | 0.5 ± 0.02 | 0.1 ± 0.00 | 0.03 ± 0.00 |
| *Cronobacter sakazakii* (Gene Accession No. WP_029039499) | | | | |
| 1426 | L73G/S139G/G462D | 0.5 ± 0.46 | 0.02 ± 0.01 | 0.11 ± 0.11 |
| 1427 | H97A/S139G/N167G/P169A/G462D | 0.5 ± 0.02 | 0.9 ± 0.01 | 0.5 ± 0.07 |
| 1428 | H97A/S139G/G462D | 0.5 ± 0.01 | 0.06 ± 0.01 | 0.04 ± 0.01 |
| 1429 | S139G/G462D | 1.0 ± 0.02 | 0.03 ± 0.01 | 0.00 |

Codons of 13 additional amino acids that included six histidine's were fused upstream of the codon of Met-1 of each IPMS gene sequence. Such a modification allowed expression of a His-tagged IPMS having 13 additional amino acids on the N-terminus. To the resulting modified gene, additional bases were added to introduce a NcoI and a SacI restriction site at the 5'- and 3'-end, respectively, for cloning purposes. The whole DNA sequence was chemically synthesized and cloned into the *E. coli* expression vector, pETDuet-1 at the NcoI and SacI sites by SGI Inc. His-tagged IPMSs were heterologously expressed in *E. coli* BL21 (DE3) cells and purified using Co-NTA chromatography. It is noted that none of the Sequence Listings included herein show the histidine-tag that is used, which in this case is Gly-Ser-Ser-His-His-His-His-His-His-Ser-Ser.

Each of the engineered isopropylmalate synthase variants was expressed, purified, and then evaluated for activity against three substrates, which are 2-ketobutyrate (i.e., 2-KBut), 2-ketohexanoate (i.e., 2-KHex), and 2-ketooctanoate (i.e., 2-KOct). 2-KBut is the natural substrate of isopropylmalate synthase and is formed in the microbial organisms during the biosynthesis of leucine. The 2-KHex and 2-KOct are non-natural substrates of isopropylmalate synthase that would be formed inside the cells during $C_7$-$C_{11}$ 2-ketoacid, for example, 2-ketononanoate, biosynthesis.

For expressing isopropylmalate synthases and its variants, competent cells of *E. coli* BL21(DE3) cells (acquired from EMD Biosciences) were transformed using standard procedures with the pETDuet expression vector containig their gene sequences. Cells harboring the expression vector were selected on LB agar plates containing 50 μg/mL of ampicillin. A starter culture was started by transferring a single colony of transformant into 50 mL of LB medium containing 100 μg/mL of ampicillin and incubated at 37° C. with shaking at 220 rpm overnight. On the next day, 7 mL of starter culture was inoculated into 800 mL of Terrific Broth (TB) and the culture was incubated at 37° C. until it reached an OD$_{600\ nm}$ of 0.5. Isopropyl β-D-1-thiogalacto-pyranoside (IPTG) at a final concentration of 1 mM was added to induce the expression of the isopropylmalate synthase or its variant and the culture was transferred to a 15° C. incubator for 16 hours (h). At the end of 16 h, the culture was centrifuged at 8000 revolutions per minute (rpm) to pelletize the cells. The cell pellet was stored at −80° C. overnight before purification.

For isolation and purification of the enzyme, cell pellet taken from 400 mL of expression culture was suspended in B-PER reagent (Thermo Fisher Scientific, Inc., Rockford, Ill.) containing 1 µg/mL of DNAse (Thermo Fisher Scientific, Inc., Rockford, Ill.), 1 µg/mL of lysozyme (Thermo Fisher Scientific, Inc., Rockford, Ill.), 1 millimolar (mM) of dithiothreitol, and protease inhibitor cocktail (RPI Corp., Mount Prospect, Ill.). The suspension was rocked gently for 30 minutes (min) at room temperature and centrifuged at 15,000 times gravity (×g) for 20 min to pelletize cell debris. The supernatant was separated and incubated with 5 mL of Co-NTA resin (Thermo Fisher Scientific, Inc., Rockford, Ill.) that had been pre-equilibrated with an equilibration buffer (50 mM sodium phosphate, pH 8.0, containing 300 mM sodium chloride, 20 mM imidazole, 50 µL protease inhibitor cocktail, and 15% glycerol). Following an incubation period of 1 h at 4° C., the enzyme bound resin was washed with 5 volumes of equilibration buffer. Isopropylmalate synthase or its variants were eluted from the Co-NTA resin with equilibration buffer containing 200 mM imidazole. The eluted proteins were dialyzed against phosphate buffered saline and stored as a 20% glycerol solution at −20° C.

The evaluation of the LeuA variants was performed in two steps using the high-throughput enzyme assay described below. Initially, all the variants were tested for activity against a single high concentration of 2-KBut, 2-KHex, and 2-KOct. The spectrophotometric isopropylmalate synthase enzyme assay reported by Marcheschi et al (Marcheschi, R. J.; Li, H.; Zhang, K.; Noey, E. L.; Kim, S.; Chaubey, A.; Houk, K. N.; Liao, J. C. A synthetic recursive "+1" pathway for carbon chain elongation. *ACS chemical biology* 2012, 7, 689-697) was adapted into a high-throughput format in 96-well plates for the kinetic evaluation of the isopropylmalate synthase variants (shown in Table 1). The HTP isopropylmalate synthase assay used in this study is based on the quantitation of CoASH that is formed as one of the products during the condensation of 2-ketoacids with Acetyl-CoA. CoASH was quantitated on the basis of its reaction with Ellman's reagent (Dithio nitro benzoic acid; DTNB), where equimolar amount of 2-nitro-4-thiobenzoic acid is produced that could be monitored at 412 nm. During the HTP enzyme assay, 2 mM Acetyl-CoA (Sigma A2056) and 2 mM of a 2-keto acid (2-ketobutyric acid, 2-ketohexanoic acid, or 2-ketooctanoic acid) were incubated with 6-20 ug of isopropylmalate synthase or its variant in 50 mM HEPES pH 7.5 containing 20 mM KCl and 20 mM $MgCl_2$. The 96-well plate containing the reaction mixture was incubated at 30° C. for 15 min. The reaction was stopped by the addition of SDS solution (2% final). The amount of CoASH formed in the reaction was quantitated by the addition of 2 mM DTNB (Pierce #22582) and the amount of TNB formed was determined by measuring the absorbance of the solution at 412 nm in a BioTek Synergy plate reader. The amount of TNB formed was calculated using its extinction coefficient, $12500\ cm^{-1}M^{-1}$. The specific activity of the isopropylmalate synthase variant against the three 2-ketoacids was determined in these experiments (Table 1 and 2).

Following the initial evaluation, a more detailed kinetic analysis is performed on a select number of variants to determine the maximal rate (i.e., $k_{cat}$), Michaelis-Menten constant (i.e., $K_M$), and the catalytic efficiency of the enzyme (i.e., $k_{cat}/K_M$) for acetyl-CoA and 2-ketooctanoic acid. The reactions performed were as described above, but with minor modifications. During the determination of the kinetic parameters of acetyl-CoA (as presented in Table 3), its concentration was varied from 0-10 mM in the reaction mixture while 2-ketooctanoate was held constant at 2 mM. Similarly, during the determination of the kinetic parameters of 2-ketooctanoate (as presented in Table 4), its concentration was varied from 0-3.2 mM in the reaction mixture while acetyl-CoA was held constant at 2 mM. Isopropylmalate synthase variants that are more efficient (higher $k_{cat}/K_M$) than the wild type enzyme in condensing all or some of the 2-ketoacid substrates, such as 2-Koct, are desirable because they improve the overall efficiency of the relevant "+1" pathway.

Initial screening of the new isopropylmalate synthase variants showed that constructs 1409, 1414 and 1427 had significant activity against 2-ketohexanoate and 2-ketooctanoate (Table 1). This suggested that these enzymes were capable of making the "+1" pathway iterative and elongating 2-ketobutyrate to 2-ketononanoate in vivo. However, additional kinetic evaluation of constructs 1409 and 1414 demonstrated that these enzymes had 37- and 1.8-fold lower turnover ($k_{cat}$), respectively, than the *E. coli* enzyme (Table 3). Thus, a second round of modifications of 1409 and 1414 was initiated to improve the turnover of these variants.

A second round of engineering was undertaken to improve the turnover of constructs 1409 and 1414. However, the crystal structures of isopropylmalate synthases only showed the residues involved in the binding of 2-ketoacids, while the residues involved in the binding of acetyl CoA or those essential for the turnover were not known. Bioinformatics and homology modeling were used to locate amino acid substitutions in the catalytic domain of *E. coli* isopropylmalate synthase, 1409 and 1414.

Specifically, a homology model of the catalytic domain of constructs 1409, 1414 and *E. coli* isopropylmalate synthase was generated using the truncated isopropylmalate synthase from *Leptospira biflexa* as the template. The truncated IPMS from *L. biflexa* is 394 amino acids in length and lacked C-terminal regulatory domain (Zhang, Z.; Wu, J.; Lin, W.; Wang, J.; Yan, H.; Zhao, W.; Ma, J.; Ding, J.; Zhang, P.; Zhao, G. P. Subdomain II of alpha-isopropylmalate synthase is essential for activity: inferring a mechanism of feedback inhibition. *The Journal of biological chemistry* 2014, 289, 27966-27978). The sequence alignments of the truncated sequences of *E. coli* isopropylmalate synthase, construct 1409 and construct 1414 showed amino acid substitutions in the catalytic domains of the three proteins (FIG. 3). As shown in Table 2, additional substitutions were made in the catalytic domain of 1409 and 1414, respectively, to identify the residue(s) playing a major role in the catalytic efficiency of the enzyme. Each of the constructs listed in Table 2 was generated from the construct 1409 or 1414 using site-directed mutagenesis, expressed in *E. coli* BL21 (DE3) cells as his-tagged proteins and purified on Ni-NTA agarose chromatography. Constructs 1465, 1466, 1467, 1470 and 1472 showed 25-450% increase in 2-ketooctanoate substrate activity over the starting construct, 1409 (Table 2). Similarly, constructs 1456, 1457, and 1460 had the same or 33% higher 2-ketooctanoate activity than the corresponding, starting construct, 1414 (Table 2).

TABLE 2

Activity of isopropylmalate synthase variants from 2$^{nd}$ round of engineering

| Construct | | Activity (nmol · min$^{-1}$ · ug$^{-1}$) | |
|---|---|---|---|
| No. | Substitutions | 2-KH | 2-KO |

*Citrobacter freundii* MGH 56 (Gene Accession No. KDF09799)

| | | | |
|---|---|---|---|
| 1409 | H97A/S139G/N167G/P169A/G462D | 0.8 ± 0.01 | 0.4 ± 0.0 |
| 1462 | V123I/H97A/S139G/N167G/P169A/G462D | 0.8 ± 0.01 | 0.3 ± 0.01 |
| 1464 | K164T/H97A/S139G/N167G/P169A/G462D | 0.2 ± 0.01 | 0.10 ± 0.00 |
| 1465 | G181A/A182G/H97A/S139G/N167G/P169A/G462D | 1.1 ± 0.02 | 0.7 ± 0.01 |
| 1466 | G210A/A214S/H97A/S139G/N167G/P169A/G462D | 2.0 ± 0.00 | 0.9 ± 0.01 |
| 1467 | G181A/A182G/G210A/A214S/H97A/S139G/N167G/P169A/G462D | >3.07 | 1.8 ± 0.01 |
| 1468 | Q258H/H97A/S139G/N167G/P169A/G462D | 1.0 ± 0.00 | 0.3 ± 0.01 |
| 1469 | R260A/H97A/S139G/N167G/P169A/G462D | 0.4 ± 0.00 | 0.2 ± 0.00 |
| 1470 | Q258H/R260A/H97A/S139G/N167G/P169A/G462D | 2.4 ± 0.01 | 1.1 ± 0.01 |
| 1471 | V324I/H97A/S139G/N167G/P169A/G462D | 0.5 ± 0.00 | 0.3 ± 0.00 |
| 1472 | N349S/S352N/H97A/S139G/N167G/P169A/G462D | 1.4 ± 0.01 | 0.5 ± 0.00 |

*Enterobacter cloacae* (Gene Accession No. WP_0.14830637)

| | | | |
|---|---|---|---|
| 1414 | H97A/S139G/N167G/P169A/G462D | 4.0 ± 0.02 | 1.8 ± 0.01 |
| 1445 | H97G/S139G/N167G/P169A/G462D | 2.4 ± 0.0 | 1.6 ± 0.01 |
| 1446 | H97A/S139G/N167G/P169A/G462D | 0.7 ± 0.01 | 0.1 ± 0.00 |
| 1447 | H97G/S139G/N167G/P169A/G462D | No activity | No activity |
| 1448 | L73A/H97A/S139G/N167G/P169A/G462D | 1.6 ± 0.02 | 0.4 ± 0.01 |
| 1449 | G72A/H97A/S139G/N167G/P169A/G462D | >2.51 | 1.7 ± 0.01 |
| 1451 | T64Q/I65V/H97A/S139G/N167G/P169A/G462D | 2.8 ± 0.06 | 1.3 ± 0.01 |
| 1452 | K164T/H97A/S139G/N167G/P169A/G462D | 3.4 ± 0.02 | 1.5 ± 0.00 |
| 1453 | D149A/H97A/S139G/N167G/P169A/G462D | >2.9 | 1.5 ± 0.01 |
| 1454 | S181A/N182G/T185S/H97A/S139G/N167G/P169A/G462D | >1.2 | 1.2 ± 0.04 |
| 1455 | A214S/I215L/H97A/S139G/N167G/P169A/G462D | 0.08 ± 0.01 | 0.01 ± 0.00 |
| 1456 | R260A/N264Q/H97A/S139G/N167G/P169A/G462D | >2.7 | 1.8 ± 0.02 |
| 1457 | M255L/R260A/N264Q/H97A/S139G/N167G/P169A/G462D | >2.8 | 2.0 ± 0.04 |
| 1459 | E342D/D348E/D350E/H97A/S139G/N167G/P169A/G462D | 2.7 ± 0.04 | 1.2 ± 0.01 |
| 1460 | D348E/D350E/M353L/Q355N/H97A/S139G/N167G/P169A/G462D | >3.4 | 2.4 ± 0.02 |

Catalytic efficiencies ($k_{cat}/K_M$) of select constructs listed in Table 2 for acetyl CoA and 2-ketooctanoate were compared with the construct disclosed by Liao et al., U.S. Pat. No. 8,298,798 (Tables 3 and 4). Construct 1467 was found to be 21- and 9-fold more efficient than its parent construct, 1409, in capturing acetyl CoA and 2-ketooctanoate for catalysis (Table 3 and 4). It was also 30-40% more efficient than the previousy disclosed *E. coli* isopropylmalate synthase construct (construct 614), in capturing both acetyl CoA and 2-ketooctanoate for catalysis (Table 3 and 4). Constructs 1457 and 1460 were also better than their parent construct, 1414, as well as the previously disclosed *E. coli* isopropylmalate synthase (construct 614), as catalysts (Table 3 and 4).

TABLE 3

Kinetic Parameters of acetyl CoA for isopropylmalate synthase variants.

| Construct | $K_i$, mM | $K_M$, mM | $k_{cat}$, min$^{-1}$ | $k_{cat}/K_M$, min$^{-1}$ mM$^{-1}$ |
|---|---|---|---|---|
| *E. coli* (Gene Accession No. EG11226) | | | | |
| 614 | 33 ± 5.3 | 0.83 ± 0.05 | 264 ± 8 | 322 ± 23 |
| *Citrobacter freundii* MGH 56 (Gene Accession No. KDF09799) | | | | |
| 1409 | — | 0.45 ± 0.24 | 7.1 ± 1.2 | 19 ± 12 |
| 1465 | 26 ± 6.3 | 0.65 ± 0.13 | 106 ± 6 | 170 ± 35 |
| 1466 | 17 ± 6 | 0.66 ± 0.14 | 24 ± 2.4 | 38 ± 8.8 |
| 1467 | 25 ± 5 | 0.74 ± 0.07 | 312 ± 15 | 423 ± 47 |
| *Enterobacter cloacae* (Gene Accession No. WP_014830637) | | | | |
| 1414 | 59 ± 18 | 0.64 ± 0.05 | 141 ± 5 | 218 ± 19 |
| 1457 | 51 ± 9.5 | 0.72 ± 0.04 | 230 ± 5 | 318 ± 18 |
| 1460 | 41 ± 5.7 | 0.67 ± 0.12 | 206 ± 16 | 318 ± 59 |

TABLE 4

Kinetic parameters of isopropylmalate synthase variants for 2-Ketooctanoic acid.

| Construct | Substitution | $K_M$, mM | $k_{cat}$, min$^{-1}$ | $k_{cat}/K_M$, min$^{-1}$·mM$^{-1}$ |
|---|---|---|---|---|
| *E. coli* (Gene Accession No. EG11226) | | | | |
| 614 | H97A/S139G/N167G/P169A/G462D | 0.25 ± 0.035 | 272 ± 18 | 1113 ± 117 |
| *Citrobacter freundii* MGH 56 (Gene Accession No. KDF09799) | | | | |
| 1409 | H97A/S139G/N167G/P169A/G462D | 0.064 ± 0.009 | 12.3 ± 0.5 | 176 ± 18 |
| 1467 | G181A/A182G/G210A/A214S/H97A/S139G/N167G/P169A/G462D | 0.092 ± 0.009 | 148 ± 5 | 1587 ± 118 |
| *Enterobacter cloacae* (Gene Accession No. WP_014830637) | | | | |
| 1414 | H97A/S139G/N167G/P169A/G462D | 0.124 ± 0.008 | 168 ± 3.9 | 1355 ± 59 |
| 1457 | M255L/R260A/N264Q/H97A/S139G/N167G/P169A/G462D | 0.176 ± 0.009 | 247 ± 5.4 | 1413 ± 59 |
| 1460 | D348E/D350E/M353L/Q355N/H97A/S139G/N167G/P169A/G462D | 0.170 ± 0.007 | 210 ± 3.5 | 1237 ± 59 |

In Vivo Production of $C_4$-$C_8$ Alcohols in Engineered Strains of *E. Coli* Using isopropylmalate Synthase Variants in Combination with the '+1 Pathway' Enzymes.

Strain Construction

The effects of isopropylmalate synthase variants on alcohol production was evaluated in an engineered MG1655 strain of *Escherichia coli* (*E. coli*). MG1655 strain was modified to improve linear alcohol production, enable expression of the genes from the Plac promoters and impart clonal stability. Improvements for linear alcohol production involved knocking down of the ilvBN and ilvIH genes, and upregulation of the ilvA gene in *E. coli* MG1655. Knock-out of ilvBN and ilvIH genes eliminated branched chain alcohol production, while upregulation of the ilvA gene increased the production of 2-ketobutyrate. Upregulation of ilvA was effected by replacing its native promoter and ribosome binding site with a strong constitutive promoter, BBa_J23119 and a synthetic ribosome binding site, BBa_B0034. Both the strong constitutive promoter and the synthetic ribosome binding site were obtained from the Registry of Standard Biological Parts (htttp//parts.igem.org), a database of biological parts curated by iGEM (International Genetically Engineered Machine Competition). The knocking down of the ilvBN and ilvIH genes and the replacement of the native promoter and ribosome binding site of ilvA gene was performed via lambda(red)-mediated recombination as described by Datsenko and Wanner (PNAS 97(12):6640-6645). To enable expression of the genes from the Plac promoters, the DE3 lysogen was integrated into MG1655 using the λDE3 Lysogenization Kit (EMD Millipore Cat #69734). To ensure clonal stability, recA was inactivated by λRed-mediated homologous recombination. The genotype of the resulting strain that was used for the alcohol production studies was MG1655(DE3) ΔrecA ΔilvBN ΔilvIH ilvAup.

Vector Construction

During the evaluation of the effects of isopropylmalate synthase variants on $C_4$-$C_8$ alcohol production in the engineered MG1655 E. coli strain, the following six enzymes were coexpressed: i) Native E. coli isopropylmalate synthase (LeuA; GenBank: Accession No. NC 000913.3 Gene ID: 947465), ii) native E. coli isopropylmalate isomerase (LeuCD; GenBank: Accession No. NC 000913.3 Gene ID: 94576 and Gene ID: 945642), iii) isopropylmalate synthase variants described in Table 5, iv) E. coli isopropylmalate dehydrogenase (LeuB; GenBank: Accession NO. NC 000913.3 Gene ID: 944798), v) F381L/V461A variant of ketoisovalerate decarboxylase (KIVD*) from Lactocossus lactis (described by Zhang et. al PNAS. 2008, 105, 20653-20658), and vi) S. cerevisiae alcohol dehydrogenase (ADH6; GenBank: Accession No. NC_001145.3 GeneID: 855368).

TABLE 5

Vectors containing the isopropylmalate synthase variant genes constructed for the evaluation of the effects on alcohol composition in the engineered MG1655 strain.

| Variant number | Plasmid ID |
| --- | --- |
| 614 | pSD-0100 |
| 1414 | pSD-0135 |
| 1457 | pSD-0136 |
| 1460 | pSD-0137 |
| 1409 | pSD-0138 |
| 1466 | pSD-0139 |
| 1467 | pSD-0140 |

Figure 4:
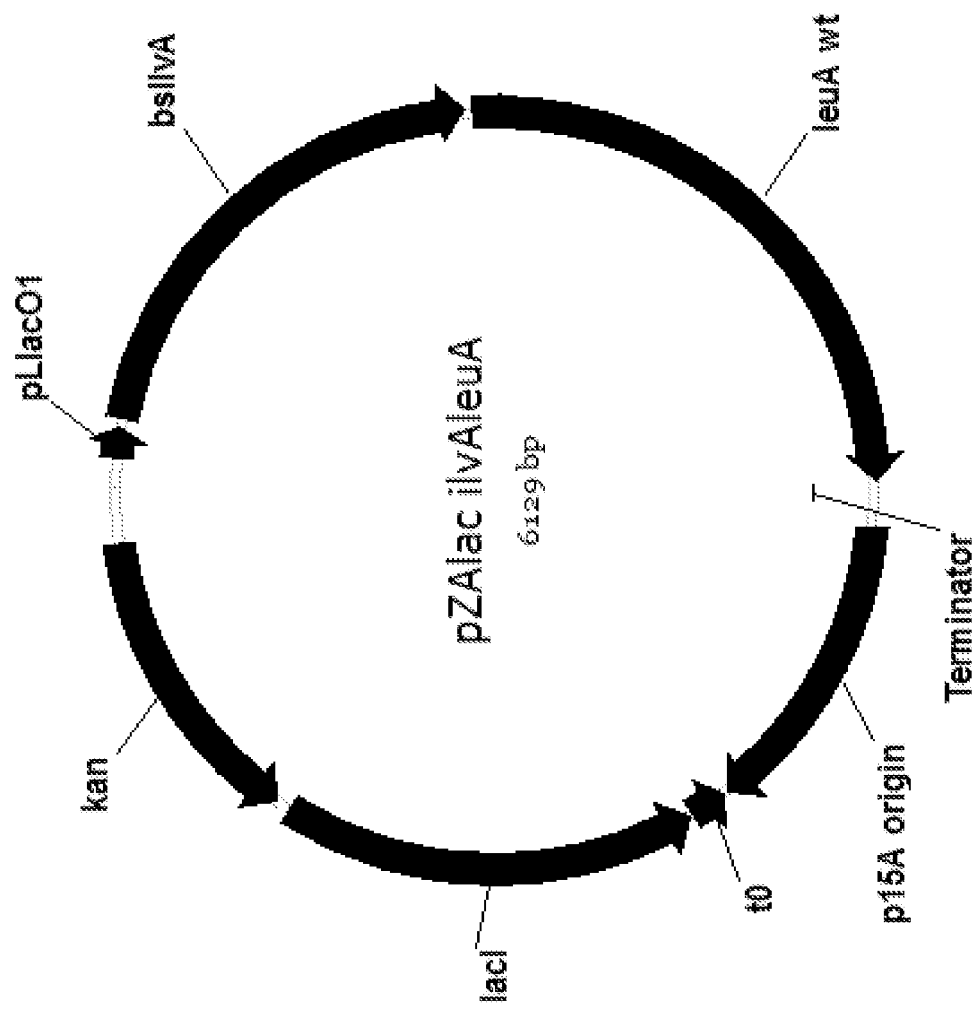
FIG. 4. The pZAlac_ilvAleuA vector. Shown is the pZAlac_ilvAleuA vector that was used for the alcohol production studies.
Figure 5:
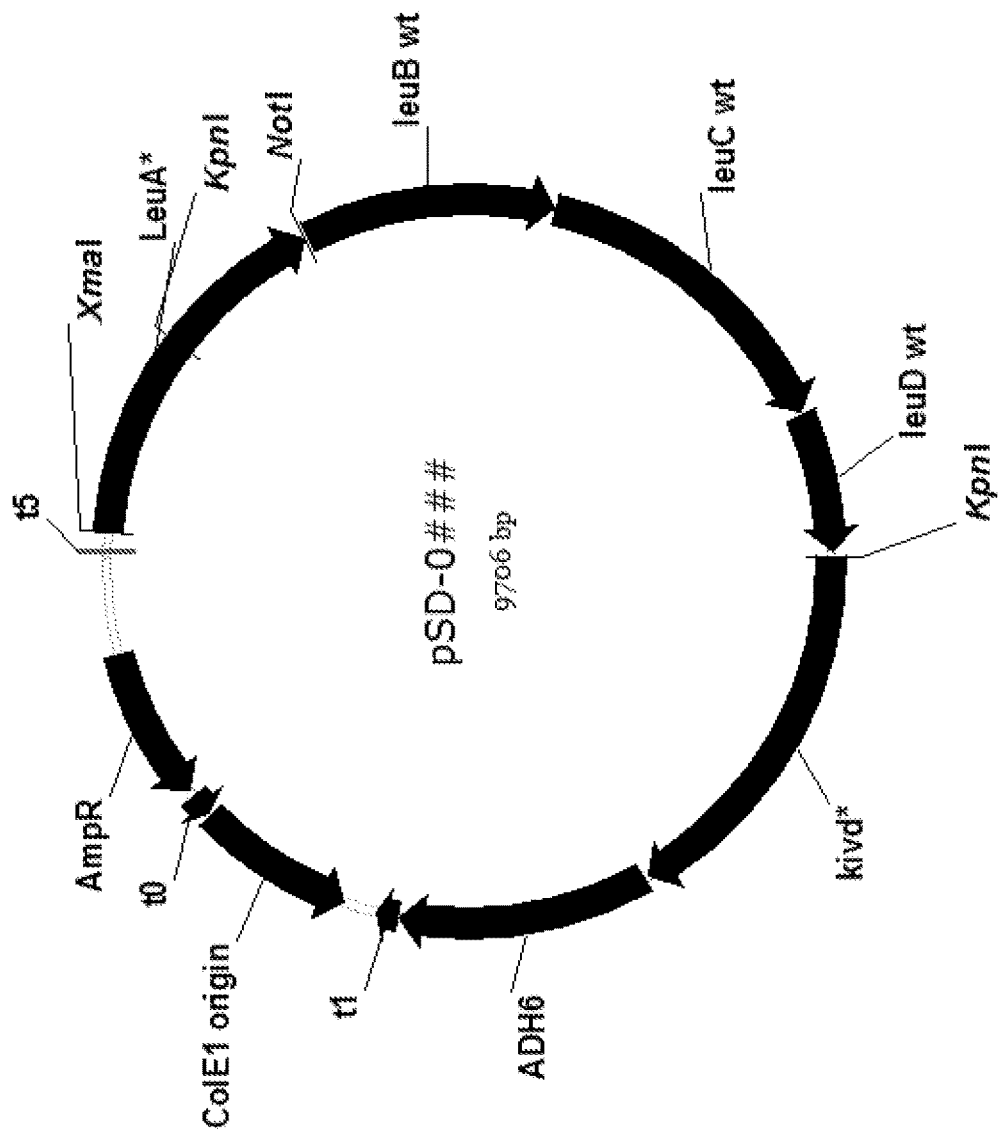
FIG. 5. The pSD-0 ###vector. Shown is a typical modified pSD-0 ###vector that was used for the alcohol production studies.

All the enzymes were expressed using the two expression vectors, pZE_LeuABCD-KA6 and pZAlac_ilvAleuA described by Marcheschi et al (ACS Chem. Biol. 2012, 7, 689-697) and acquired from Dr. James C. Liao's group at UCLA. pZAlac_ilvAleuA (FIG. 4) contained a copy of ilva and wild type LeuA gene, and was used without any further modification. pZE_LeuABCD-KA6 was modified to express the isopropylmalate synthase variants described in Table 5 along with LeuB, LeuC, LeuD, and KiVD* (F381L/V461A variant of ketoisovalerate decarboxylase from Lactocossus lactis described by Zhang et. al PNAS. 2008, 105, 20653-20658) genes. Six vectors containing different isopropylmalate synthase variant genes (shown in Table 5) were constructed for these studies. FIG. 5 shows a typical modified vector, pSD-0 ###, that was used along with pZAlac_ilvAleuA for the alcohol production studies. As shown in FIG. 4 and listed in Table 5, each pSD-0 ###vector expressed a given isopropylmalate synthase variant in the transformed cells. All the genes in both the vectors were under pLacO1 promoter and induced using Isopropyl β-D-1-thiogalactopyranoside (IPTG).

Figure 6:
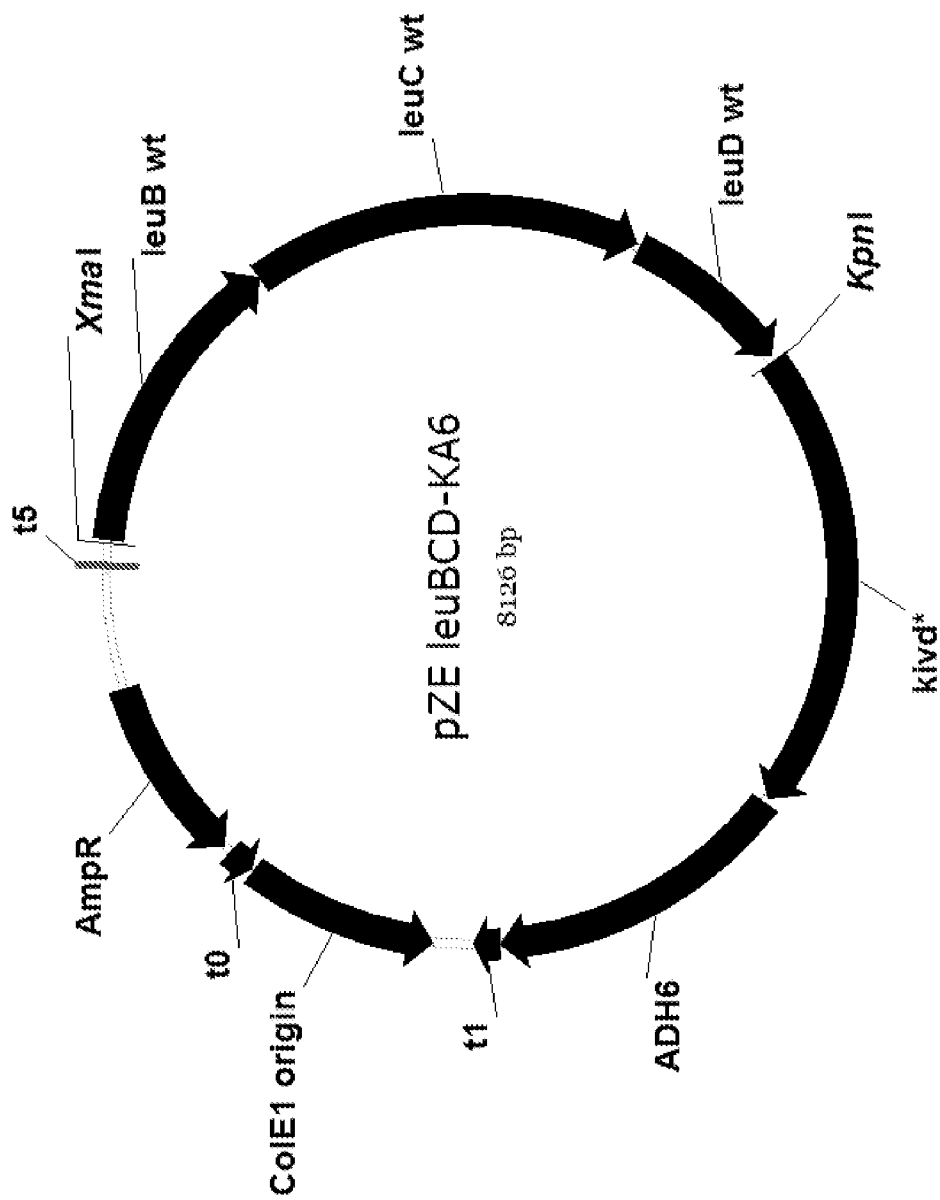
FIG. 6. The pZE BCD-KA6 vector. Shown is the pZE BCD-KA6 vector that was used for the alcohol production studies.

The genes of isopropylmalate synthase variants were cloned into the pZE_LeuABCD-KA6 vector using the Gibson assembly technology of New England Bioscience. Initially, LeuABCD genes were removed from the pZE_LeuABCD-KA6 vector using the restriction enzyme KpnI. Genes LeuBCD were reinserted into the cut vector along with a unique XmaI cut site, to generate an intermediate vector, pZE BCD-KA6 (shown in FIG. 6) using Gibson assembly. In the second step, PCR generated isopropylmalate synthase gene was inserted into the pZE BCD-KA6 vector at the XmaI site using Gibson Assembly to generate the final pSD-0 ###vector. For alcohol production, the engineered MG1655 strain of E. coli (MG1655(DE3) ΔrecA ΔilvBN ΔilvIH ilvAup) was transformed with the pZAlac_ilvAleuA vector (FIG. 4) and one of the pSDL-0 ###vector listed in Table 5.

Alcohol Production in Engineered MG1655 Cells

MG1655 strains transformed with the pZAlac_ilvAleuA and one of the pSDL-0 ###vectors listed in Table 5 were selected on LB agar plates containing 100 ug/mL ampicillin and 25 ug/mL kanamycin. A 50 mL starter culture in LB medium containing 100 ug/mL ampicillin and 25 ug/mL kanamycin was initiated using a single colony from the dual antibiotic LB agar plate and incubated overnight at 37° C. in an incubator shaker set at 200 rpm. After 12-16 hours of incubation, serum bottles containing 5 mL of sterile modified 2×M9 medium (composition shown in Table 6) with 100 ug/mL ampicillin and 25 ug/ml kanamycin were inoculated with 50 uL of starter culture.

TABLE 6

Medium composition used to demonstrate alcohol production from E. coli recombinantly engineered to contain the '+1 pathway' in combination with isopropylmalate synthase variants.
2X M9 Medium

| | Conc (g/L) |
| --- | --- |
| NA2HPO4 | 13.56 |
| KH2PO4 | 6 |
| NH4Cl | 2 |
| NaCl | 1 |
| Yeast Extract | 10 |
| Glucose | 40 |
| 92949 Trace Metal Mix A5 w/ Co | 1 |

Cultures were incubated at 37° C. with shaking at 200 rpm and induced after 3 hrs using 0.1 mM of IPTG to express all the genes. The culture temperature was reduced to 30° C. after induction. Cultures were harvested 44 hours after induction by transferring them to 4° C. for 20-30 minutes. Serum bottles were then de-capped, and the fermentation broth was quickly poured into a 15 mL conical tube containing 1 mL of a saturated sodium chloride solution and 2 mL of analytical grade toluene. The broth-sodium chloride-toluene mixture was vortexed for 30 seconds and the toluene extract was subjected to alcohol analysis using a GC/FID method described in WO2016094604 A1, which is incorporated herein by reference in its entirety.

Table 7 shows the effects of the five isopropylmalate synthase variants on the alcohol composition in the strains expressing them along with the other genes mentioned above. All five of the isopropylmalate synthase variants expressing cells produced significant heptanol titers. This indicates that the isopropylmalate synthase variants are active inside the cells, since the longest alcohol produced by strains expressing only the wild type LeuA is hexanol (Marcheschi et al ACS Chem. Biol. 2012, 7, 689-697). Comparable levels of heptanol produced in strains expressing 614, 1409 and 1467 suggests that under the experimental conditions used here, 1409 and 1467 can effectively substitute for 614 in the non-natural pathway

TABLE 7

The mean alcohol titers for serum bottle fermentations of E. coli containing the '+1 pathway' enzymes in combination with the variant isopropylmalate synthase enzymes.

| Variant # | 1-Butanol | 1-Pentanol | 1-Hexanol | 1-Heptanol | Total Alcohols |
|---|---|---|---|---|---|
| 1409 | 270.2 ± 12.2 | 356.0 ± 11.4 | 194.0 ± 1.8 | 45.3 ± 5.0 | 865.5 ± 8.2 |
| 1467 | 272.9 ± 10.3 | 366.4 ± 31.6 | 209.5 ± 19.8 | 42.0 ± 4.3 | 890.8 ± 65.6 |
| 1414 | 275.0 ± 18.9 | 528.6 ± 47.1 | 166.1 ± 27.9 | 14.6 ± 5.9 | 984.4 ± 93.4 |
| 1457 | 302.6 ± 8.5 | 541.2 ± 26.6 | 200.3 ± 0.9 | 25.7 ± 7.1 | 1069.8 ± 16.4 |
| 1460 | 262.9 ± 15.1 | 621.4 ± 38.6 | 197.5 ± 19.2 | 18.8 ± 4.6 | 1100.7 ± 77.4 |
| 614 | 260.7 ± 8.6 | 369.3 ± 12.4 | 205.6 ± 7.7 | 65.2 ± 1.7 | 900.9 ± 29.8 |

* ADH6 and kivD were also included in all strain constructs. All titers are shown in milligrams per liter ± standard deviation across a minimum of triplicate experiments. Titers were measured 44 hours after induction.

In summary, several isopropylmalate synthases that are as good as or better than the patented *E. coli* isopropylmalate synthase are available for developing strains capable of producing 2-ketoacids of varied lengths. Furthermore, constructs 1409 and 1414 and their variants listed in Table 3 and Table 4 constitute a list of isopropylmalate synthases that become more efficient in condensing 2-ketoacids and acetyl CoA. Together, they offer a battery of isopropylmalate synthases that offer an opportunity to match the flux through the "+1" pathway with acetyl CoA availability/demand in a given microorganism and allow optimization of 2-ketoacid elongation.

What is claimed is:

1. A process for preparing a $C_7$-$C_{11}$ 2-ketoacid, the process comprising: (I) providing at least one of a $C_4$-$C_{10}$ 2-ketoacid substrate, with:
   (a) a genetically modified isopropylmalate synthase (IPMS) comprising at least one of:
   (i) an isopropylmalate synthase variant comprising the amino acid sequence variant of SEQ ID NO: 1 having mutations H97A, S139G, N167G, P169A, G181A, A182G, G210A, A214S, and G462D in the SEQ ID NO: 1 and having IPMS activity; (ii) isopropylmalate synthase variant comprising the amino acid sequence variant comprising SEQ ID NO: 2 having the mutations H97A, S139G, N167G, P169A, M255L, R260A, N264Q, and G462D in the SEQ ID NO: 2 and having IPMS activity; or (iii) isopropylmalate synthase variant comprising the amino acid sequence variant of comprising SEQ ID NO: 2 having the mutations H97A, S139G, N167G, P169A, D348E, D350E, M353L, Q355N, and G462D in the SEQ ID NO: 2 and having IPMS activity
   (b) a isopropylmalate isomerase having isopropylmalate isomerase activity; and
   (c) a isopropylmalate dehydrogenase having isopropylmalate dehydrogenase activity;
   under conditions that the at least one of the $C_4$-$C_{10}$ 2-ketoacid substrate is converted to the $C_7$-$C_{11}$ 2-ketoacid; and wherein the conversion of the at least one of the $C_4$-$C_{10}$ 2-ketoacid substrate to the $C_7$-$C_{11}$ 2-ketoacid occurs via one or more biochemical reactions.

2. The process according to claim 1, wherein the at least one of the $C_4$-$C_{10}$ 2-ketoacid substrate comprises 2-ketobutyrate.

3. The process according to claim 1, wherein the at least one of the $C_4$-$C_{10}$ 2-ketoacid substrate comprises 2-ketoisovalerate.

4. A genetically modified isopropylmalate synthase (IPMS) polypeptide having isopropylmalate synthase activity, the polypeptide comprising at least one of: (a) an isopropylmalate synthase variant comprising the amino acid sequence variant of SEQ ID NO: 1 having mutations H97A, S139G, N167G, P169A, G181A, A182G, G210A, A214S, and G462D in the SEQ ID NO: 1 and having IPMS activity; (b) isopropylmalate synthase variant comprising the amino acid sequence variant comprising SEQ ID NO: 2 having the mutations H97A, S139G, N167G, P169A, M255L, R260A, N264Q, and G462D in the SEQ ID NO: 2 and having IPMS activity; or (c) isopropylmalate synthase variant comprising the amino acid sequence variant of comprising SEQ ID NO: 2 having the mutations H97A, S139G, N167G, P169A, D348E, D350E, M353L, Q355N, and G462D in the SEQ ID NO: 2 and having IPMS activity.

5. The genetically modified isopropylmalate synthase polypeptide having isopropylmalate synthase activity of claim 4, wherein the polypeptide comprises the isopropylmalate synthase variant comprising the amino acid sequence variant of SEQ ID NO: 1 having mutations H97A, S139G, N167G, P169A, G181A, A182G, G210A, A214S, and G462D in the SEQ ID NO: 1 and having IPMS activity.

6. The genetically modified isopropylmalate synthase polypeptide having isopropylmalate synthase activity of claim 4, wherein the polypeptide comprises the isopropylmalate synthase variant comprising the amino acid sequence variant comprising SEQ ID NO: 2 having the mutations H97A, S139G, N167G, P169A, M255L, R260A, N264Q, and G462D in the SEQ ID NO: 2 and having IPMS activity.

7. The genetically modified isopropylmalate synthase polypeptide having isopropylmalate synthase activity of claim 4, wherein the polypeptide comprises the isopropylmalate synthase variant comprising the amino acid sequence variant of comprising SEQ ID NO: 2 having the mutations H97A, S139G, N167G, P169A, D348E, D350E, M353L, Q355N, and G462D in the SEQ ID NO: 2 and having IPMS activity.

* * * * *